(12) United States Patent
Baker et al.

(10) Patent No.: US 10,526,391 B2
(45) Date of Patent: Jan. 7, 2020

(54) MOLECULAR CONSTRUCTS AND USES THEREOF

(71) Applicants: THE UNIVERSITY OF NOTRE DAME DU LAC, Notre Dame, IN (US); University of Massachusetts, Boston, MA (US)

(72) Inventors: Brian Baker, Granger, IN (US); Lance Hellman, Granger, IN (US); Brian Pierce, Darnestown, MD (US); Zhiping Weng, Wellesley, MA (US)

(73) Assignees: The University of Notre Dame du Lac, Notre Dame, IN (US); University of Massachusetts, Boston, MA (US)

( * ) Notice: Subject to any disclaimer, the term of this patent is extended or adjusted under 35 U.S.C. 154(b) by 445 days.

(21) Appl. No.: 15/327,984

(22) PCT Filed: Jul. 22, 2015

(86) PCT No.: PCT/US2015/041625
§ 371 (c)(1),
(2) Date: Jan. 20, 2017

(87) PCT Pub. No.: WO2016/014725
PCT Pub. Date: Jan. 28, 2016

(65) Prior Publication Data
US 2017/0333524 A1 Nov. 23, 2017

Related U.S. Application Data

(60) Provisional application No. 62/027,451, filed on Jul. 22, 2014.

(51) Int. Cl.
| | |
|---|---|
| *C07K 14/725* | (2006.01) |
| *C12N 5/0783* | (2010.01) |
| *C12N 15/86* | (2006.01) |
| *A61K 35/17* | (2015.01) |
| *A61K 38/17* | (2006.01) |
| *A61K 35/12* | (2015.01) |

(52) U.S. Cl.
CPC .......... *C07K 14/7051* (2013.01); *A61K 35/17* (2013.01); *A61K 38/1774* (2013.01); *C12N 5/0636* (2013.01); *C12N 15/86* (2013.01); *A61K 2035/124* (2013.01); *C12N 2510/00* (2013.01)

(58) Field of Classification Search
CPC .. C07K 14/7051; C12N 15/86; C12N 5/0636; C12N 2510/00; C12N 15/62; A61K 35/17; A61K 38/1774; A61K 2035/124; A61K 31/7088
USPC ........... 530/350, 837, 402; 435/320.1
See application file for complete search history.

(56) References Cited

U.S. PATENT DOCUMENTS

| | | | |
|---|---|---|---|
| 4,873,190 A | 10/1989 | Saito et al. |
| 4,874,845 A | 10/1989 | Saito et al. |
| 4,946,778 A | 8/1990 | Ladner et al. |
| 4,970,296 A | 11/1990 | Saito et al. |
| 5,223,409 A | 6/1993 | Ladner et al. |
| 5,258,498 A | 11/1993 | Huston et al. |
| 5,260,203 A | 11/1993 | Ladner et al. |
| 5,580,961 A | 12/1996 | Saito et al. |
| 5,614,192 A | 3/1997 | Vandenbark |
| 5,733,743 A | 3/1998 | Johnson et al. |
| 5,780,225 A | 7/1998 | Wigler et al. |
| 5,789,208 A | 8/1998 | Sharon |
| 5,830,755 A | 11/1998 | Nishimura et al. |
| 5,837,477 A | 11/1998 | Germain et al. |
| 5,840,304 A | 11/1998 | Davis et al. |
| 5,882,945 A | 3/1999 | Saito et al. |
| 5,977,321 A | 11/1999 | Saito et al. |
| 6,140,120 A | 10/2000 | Crabtree et al. |
| 6,165,787 A | 12/2000 | Crabtree et al. |
| 6,270,772 B1 | 8/2001 | Burrows et al. |
| 6,300,065 B1 | 10/2001 | Kieke et al. |
| 6,319,713 B1 | 11/2001 | Patten et al. |
| 6,416,971 B1 | 7/2002 | Reinhertz et al. |
| 6,423,538 B1 | 7/2002 | Wittrup et al. |

(Continued)

OTHER PUBLICATIONS

Borbulevych et al. (2011) J. Immunol., vol. 187(5), 2453-2563.*

(Continued)

*Primary Examiner* — Anne Marie S Wehbe
(74) *Attorney, Agent, or Firm* — Michael Best & Friedrich LLP

(57) ABSTRACT

Molecular constructs and dual recognition constructs having a sequence encoding a TCR affinity weakening motif, and DNA and RNA sequences corresponding thereto, are presented. Modified T-cells and other cells transformed with the molecular contracts express a modified TCR that imparts a reduction, in non-specific binding, -an enhancement of binding specificity and an enhancement of binding affinity for a target antigen, compared to non-transformed (wild-type, native) T-cells, are described. The modified TCRs possess an affinity enhancing motif and an affinity weakening motif. Methods of transforming cells and methods of using enriched populations of transformed cells, in the treatment of cancer and infections arid T-cell mediated pathologies are provided. The affinity weakening motif imparts a weakened interaction, of a TCR with major histocompatibility complex proteins, such as HLA proteins in humans. Soluble modified TCRs are also provided, Therapeutic preparations comprising modified T-cells, modified TCRs, and modified TCR-therapeutic agent-conjugates, are also provided.

17 Claims, 6 Drawing Sheets
Specification includes a Sequence Listing.

(56) References Cited

U.S. PATENT DOCUMENTS

| | | |
|---|---|---|
| 6,682,736 B1 | 1/2004 | Hanson et al. |
| 6,696,251 B1 | 2/2004 | Wittrup et al. |
| 6,699,658 B1 | 3/2004 | Wittrup et al. |
| 6,759,243 B2 | 7/2004 | Kranz et al. |
| 6,805,861 B2 | 10/2004 | Stauss |
| 6,815,171 B2 | 11/2004 | Burrows et al. |
| 6,838,290 B2 | 1/2005 | Sims et al. |
| 6,864,359 B1 | 3/2005 | Luo |
| 6,951,917 B1 | 10/2005 | Topalian et al. |
| 6,972,193 B1 | 12/2005 | Crabtree et al. |
| 7,109,003 B2 | 9/2006 | Hanson et al. |
| 7,115,361 B2 | 10/2006 | Lalvani et al. |
| 7,166,707 B2 | 1/2007 | Feige |
| 7,169,905 B2 | 1/2007 | Feige |
| 7,186,810 B2 | 3/2007 | Feige |
| 7,189,827 B2 | 3/2007 | Feige |
| 7,261,894 B2 | 8/2007 | Sims et al. |
| 7,265,218 B2 | 9/2007 | Burrows et al. |
| 7,329,731 B2 | 2/2008 | Jakobsen et al. |
| 7,355,008 B2 | 4/2008 | Stavenhagen et al. |
| 7,465,787 B2 | 12/2008 | Wittrup et al. |
| 7,501,501 B2 | 3/2009 | Topalian et al. |
| 7,557,190 B2 | 7/2009 | Barbosa et al. |
| 7,569,357 B2 | 8/2009 | Kranz et al. |
| 7,576,183 B2 | 8/2009 | Gupta et al. |
| 7,608,410 B2 | 10/2009 | Dunn et al. |
| 7,632,497 B2 | 12/2009 | Stavenhagen |
| 7,871,817 B2 | 1/2011 | Voss et al. |
| 7,894,995 B2 | 2/2011 | Jojic et al. |
| 7,915,036 B2 | 3/2011 | Morgan et al. |
| 7,960,512 B2 | 6/2011 | Stavenhagen et al. |
| 8,088,379 B2 | 1/2012 | Robbins et al. |
| 8,143,376 B2 | 3/2012 | Boulter et al. |
| 8,143,379 B2 | 3/2012 | Hanson et al. |
| 8,192,737 B2 | 6/2012 | Stavenhagen et al. |
| 8,193,321 B2 | 6/2012 | Bostrom et al. |
| 8,216,574 B2 | 7/2012 | Stavenhagen et al. |
| 8,217,147 B2 | 7/2012 | Stavenhagen et al. |
| 8,293,237 B2 | 10/2012 | Burkly et al. |
| 8,372,636 B2 | 2/2013 | Wittrup et al. |
| 8,378,074 B2 | 2/2013 | Jakobsen et al. |
| 8,383,364 B2 | 2/2013 | Berkhout et al. |
| 8,383,401 B2 | 2/2013 | Shiku et al. |
| 8,409,577 B2 | 4/2013 | Thompson et al. |
| 8,461,306 B2 | 6/2013 | Williams et al. |
| 8,491,895 B2 | 7/2013 | Hanson et al. |
| 8,491,913 B2 | 7/2013 | Offner et al. |
| 8,519,100 B2 | 8/2013 | Jakobsen et al. |
| 8,530,627 B2 | 9/2013 | Koenig et al. |
| 8,552,150 B2 | 10/2013 | Yang et al. |
| 8,586,714 B2 | 11/2013 | Ghayur et al. |
| 8,617,845 B2 | 12/2013 | Gallo et al. |
| 8,652,466 B2 | 2/2014 | Stavenhagen et al. |
| 8,691,730 B2 | 4/2014 | Vasquez et al. |
| 8,697,071 B2 | 4/2014 | Stavenhagen et al. |
| 8,716,450 B2 | 5/2014 | Ghayur et al. |
| 8,722,855 B2 | 5/2014 | Ghayur et al. |
| 8,735,546 B2 | 5/2014 | Ghayur et al. |
| 8,741,860 B2 | 6/2014 | Li et al. |
| 8,784,808 B2 | 7/2014 | Johnson et al. |
| 8,784,823 B2 | 7/2014 | Burkly et al. |
| 8,785,599 B2 | 7/2014 | Johnson et al. |
| 8,785,601 B2 | 7/2014 | Rosenberg et al. |
| 8,802,093 B2 | 8/2014 | Johnson et al. |
| 8,822,645 B2 | 9/2014 | Ghayur et al. |
| 2002/0058253 A1 | 5/2002 | Kranz et al. |
| 2002/0165149 A1 | 11/2002 | Kranz et al. |
| 2002/0172979 A1 | 11/2002 | Nicolette |
| 2002/0176864 A1 | 11/2002 | Burrows et al. |
| 2003/0007978 A1 | 1/2003 | Burrows et al. |
| 2003/0036506 A1 | 2/2003 | Kranz et al. |
| 2003/0036644 A1 | 2/2003 | Ulrich |
| 2004/0146952 A1 | 7/2004 | Kranz et al. |
| 2004/0146976 A1 | 7/2004 | Wittrup et al. |
| 2005/0064526 A1 | 3/2005 | Ulrich et al. |
| 2005/0074853 A1 | 4/2005 | Burrows et al. |
| 2005/0136402 A1 | 6/2005 | Wang et al. |
| 2005/0249723 A1 | 11/2005 | Lazar |
| 2005/0260222 A1 | 11/2005 | Gupta et al. |
| 2006/0166314 A1 | 7/2006 | Voss et al. |
| 2006/0240033 A1 | 10/2006 | Tsuji |
| 2006/0275282 A1 | 12/2006 | Moore et al. |
| 2007/0055049 A1 | 3/2007 | Grey et al. |
| 2007/0134261 A1 | 6/2007 | Hancock et al. |
| 2007/0190533 A1 | 8/2007 | Hancock et al. |
| 2007/0192036 A1 | 8/2007 | Jojic et al. |
| 2007/0192037 A1 | 8/2007 | Jojic et al. |
| 2007/0202591 A1 | 8/2007 | Ulrich |
| 2008/0009519 A1 | 1/2008 | Steinman et al. |
| 2008/0064859 A1 | 3/2008 | Vandenbark et al. |
| 2008/0213237 A1 | 9/2008 | Frankenburg et al. |
| 2008/0260762 A1 | 10/2008 | Grey et al. |
| 2008/0267987 A1 | 10/2008 | Burrows et al. |
| 2008/0292549 A1 | 11/2008 | Jakobsen et al. |
| 2008/0299137 A1 | 12/2008 | Svendsen et al. |
| 2009/0053184 A1 | 2/2009 | Morgan et al. |
| 2009/0068226 A1 | 3/2009 | Ulrich et al. |
| 2009/0175867 A1 | 7/2009 | Thompson et al. |
| 2009/0217403 A1 | 8/2009 | Spits |
| 2009/0275137 A1 | 11/2009 | Krantz et al. |
| 2009/0280135 A1 | 11/2009 | Offner et al. |
| 2009/0280560 A1 | 11/2009 | Wittrup et al. |
| 2010/0009863 A1 | 1/2010 | Himmler et al. |
| 2010/0021468 A1 | 1/2010 | Wang et al. |
| 2010/0034834 A1 | 2/2010 | Robbins et al. |
| 2010/0093979 A1 | 4/2010 | Lazar et al. |
| 2010/0113300 A1 | 5/2010 | Jakobsen et al. |
| 2010/0158881 A1 | 6/2010 | Hwu et al. |
| 2010/0166722 A1 | 7/2010 | Bennett et al. |
| 2010/0297093 A1 | 11/2010 | Robbins et al. |
| 2011/0008382 A1 | 1/2011 | Burrows et al. |
| 2011/0014169 A1 | 1/2011 | Boulter et al. |
| 2011/0034532 A1 | 2/2011 | Li et al. |
| 2011/0217308 A1 | 9/2011 | Offner et al. |
| 2011/0243995 A1 | 10/2011 | Voss et al. |
| 2011/0262414 A1 | 10/2011 | Boulter et al. |
| 2011/0262479 A1 | 10/2011 | Burrows et al. |
| 2012/0015888 A1 | 1/2012 | Rosenberg et al. |
| 2012/0027739 A1 | 2/2012 | Jakobsen et al. |
| 2012/0071420 A1 | 3/2012 | Robbins et al. |
| 2012/0148601 A1 | 6/2012 | Ulrich et al. |
| 2012/0190828 A1 | 7/2012 | Jakobsen et al. |
| 2012/0207673 A1 | 8/2012 | Christ et al. |
| 2012/0252742 A1 | 10/2012 | Kranz et al. |
| 2013/0089541 A1 | 4/2013 | D'Angelo et al. |
| 2013/0149289 A1 | 6/2013 | Jakobsen et al. |
| 2013/0178605 A1 | 7/2013 | Blein et al. |
| 2013/0189309 A1 | 7/2013 | Jakobsen |
| 2013/0195900 A1 | 8/2013 | Dornmair et al. |
| 2013/0274203 A1 | 10/2013 | Morgan et al. |
| 2013/0280220 A1 | 10/2013 | Ahmed et al. |
| 2013/0330335 A1 | 12/2013 | Bremel et al. |
| 2013/0336977 A1 | 12/2013 | Thompson et al. |
| 2014/0031292 A1 | 1/2014 | Wittrup et al. |
| 2014/0056936 A1 | 2/2014 | Offner et al. |
| 2014/0066599 A2 | 3/2014 | Blein et al. |
| 2014/0099699 A1 | 4/2014 | Jakobsen et al. |
| 2014/0120622 A1 | 5/2014 | Gregory et al. |
| 2014/0154250 A1 | 6/2014 | Thompson et al. |
| 2014/0154252 A1 | 6/2014 | Thompson et al. |
| 2014/0187753 A1 | 7/2014 | Blein et al. |
| 2014/0206620 A1 | 7/2014 | Rosenberg et al. |
| 2014/0234218 A1 | 8/2014 | Christ et al. |
| 2014/0335053 A1 | 11/2014 | Wang et al. |
| 2014/0349855 A1 | 11/2014 | Jakobsen et al. |
| 2014/0371085 A1 | 12/2014 | Jakobsen et al. |

OTHER PUBLICATIONS

Pierce et al. (Feb. 13, 2014) PLoS Comput. Biol., vol. 10(2), e10003478, doi:10.1371/journal.pcbi. 1003478, pp. 1-11.*

Baker et al. (2012) Immunol. Rev., vol. 250, 10-31.*

Manning et al. (1998) Immunity, vol. 8, 413-425.*

(56) References Cited

OTHER PUBLICATIONS

Robbins et al. (2008) J. Immunol., vol. 180(9), 6116-6131.*

Smith et al. (2013) J. Mol. Biol., vol. 425, 4496-4507.*

Baker et al., Structural and dynamic control of T-cell receptor specificity, cross-reactivity, and binding mechanism, Immunological Reviews, 2012, pp. 10-31, vol. 250, John Wiley & Sons A/S, Singapore.

Bhati et al., The versatility of the αβ T-cell antigen receptor, Protein Science, 2014, pp. 260-272, vol. 23, Wiley-Blackwell.

Borg et al., The CDR3 regions of an immunodominant T cell receptor dictate the 'energetic landscape' of peptide-MHC recognition, Nature Immunology, Feb. 2005, pp. 171-180, vol. 6, No. 2, Nature Publishing Group.

Bowerman et al., Different Strategies Adopted by Kb and Ld to Generate T Cell Specificity Directed against Their Respective Bound Peptides, The Journal of Biological Chemistry, Nov. 20, 2009, pp. 32551-32561, vol. 284, No. 47, The American Society for Biochemistry and Molecular Biology, Inc., United States.

Bowerman et al., Engineering the binding properties of the T cell receptor:peptide:MHC ternary complex that governs T cell activity, Molecular Immunology, 2009, pp. 3000-3008, vol. 46, Elsevier Ltd.

Brophy et al., A yeast display system for engineering functional peptide-MHC complexes, Journal of Immunological Methods, 2003, pp. 235-246, vol. 272, Elsevier Science B.V.

Chervin et al., Design of T-cell receptor libraries with diverse binding properties to examine adoptive T-cell responses, Gene Therapy, 2013, pp. 634-644, vol. 20, Macmillan Publishers Limited.

Chervin et al., Engineering higher affinity T cell receptors using a T cell display system, Journal of Immunological Methods, 2008, pp. 175-184, vol. 339, Elsevier B.V.

Chlewicki et al., High-affinity, Peptide-specific T Cell Receptors can be Generated by Mutations in CDR1, CDR2 or CDR3, Journal of Molecular Biology, 2005, pp. 223-239, vol. 346, Elsevier Ltd.

Cho et al., Structural Basis of Affinity Maturation and Intramolecular Cooperativity in a Protein-Protein Interaction, Structure, Dec. 2005, pp. 1775-1787, vol. 13, Elsevier Ltd.

Cole et al., T-cell Receptor (TCR)-Peptide Specificity Overrides Affinity-enhancing TCR-Major Histocompatibility Complex Interactions, The Journal of Biological Chemistry, Jan. 10, 2014, pp. 628-638, vol. 289, No. 2, The American Society for Biochemistry and Molecular Biology, Inc., United States.

De Haan et al., Structure-based Design and Evaluation of MHC Class II Binding Peptides, Biologicals, 2001, pp. 289-292, vol. 29, The International Association for Biologicals.

Dunn et al., Directed evolution of human T cell receptor CDR2 residues by phage display dramatically enhances affinity for cognate peptide-MHC without increasing apparent cross-reactivity, Protein Science, 2006, pp. 710-721, vol. 15, Cold Spring Harbor Laboratory Press.

Goyarts et al., Point mutations in the β chain CDR3 can alter the T cell receptor recognition pattern on an MHC class I/peptide complex over a broad interface area, Molecular Immunology, 1998, pp. 593-607, vol. 35, Elsevier Science Ltd.

Haidar et al., Structure-based design of a T-cell receptor leads to nearly 100-fold improvement in binding affinity for pepMHC, Proteins, 2008, pp. 948-960, vol. 74, Wiley-Liss, Inc.

Holler et al., TCRs with high affinity for foreign pMHC show self-reactivity, Nature Immunology, Jan. 2003, pp. 55-62, vol. 4, No. 1, Nature Publishing Group.

Holler et al., In vitro evolution of a T cell receptor with high affinity for peptide/MHC, Proceedings of the National Academy of Sciences of the United States of America, May 9, 2000, pp. 5387-5392, vol. 97, No. 10, National Academy of Sciences.

Holler et al., T cell receptors: affinities, cross-reactivities, and a conformer model, Molecular Immunology, 2004, pp. 1027-1031, vol. 40, Elsevier Ltd.

Jones et al., Distinct CDR3 Conformations in TCRs Determine the Level of Cross-Reactivity for Diverse Antigens, but Not the Docking Orientation, The Journal of Immunology, 2008, pp. 6255-6264, vol. 181, The American Association of Immunologists, Inc.

Kranz, David M., T cell receptor CDRs: starring versus supporting roles, Nature Immunology, Feb. 2005, pp. 130-132, vol. 6, No. 2, Nature Publishing Group.

Lazoura et al., Non-canonical anchor motif peptides bound to MHC class I induce cellular responses, Molecular Immunology, 2009, pp. 1171-1178, vol. 46, Elsevier Ltd.

Lefranc et al., IMGT, the international ImMunoGeneTics database, Nucleic Acids Research, 1999, pp. 209-212, vol. 27, No. 1, Oxford University Press.

Lynch et al., Subtle changes in TCRα CDR1 profoundly increase the sensitivity of CD4 T cells, Molecular Immunology, 2013, pp. 283-294, vol. 53, Elsevier Ltd.

Manning et al., Alanine Scanning Mutagenesis of an αβ T Cell Receptor Mapping the Energy of Antigen Recognition, Immunity, Apr. 1998, pp. 413-425, vol. 8, Cell Press.

McBeth et al., A New Twist in TCR Diversity Revealed by a Forbidden αβ TCR, Journal of Molecular Biology, 2008, pp. 1306-1319, vol. 375, Elsevier Ltd.

Morgan et al., Cancer Regression in Patients After Transfer of Genetically Engineered Lymphocytes, Science, Oct. 6, 2006, pp. 126-129, vol. 314.

Pierce et al., Combinations of Affinity-Enhancing Mutations in a T Cell Receptor Reveal Highly Nonadditive Effects within and between Complementarity Determining Regions and Chains, Biochemistry, 2010, pp. 7050-7059, vol. 49, American Chemical Society.

Pierce et al., Computational Design of the Affinity and Specificity of a Therapeutic T Cell Receptor, PLOS Computational Biology, Feb. 2014, pp. 1-11, vol. 10, Issue 2.

Richman et al., Development of a novel strategy for engineering high-affinity proteins by yeast display, Protein Engineering, Design & Selection, 2006, pp. 255-264, vol. 19, No. 6, Oxford University Press.

Richman et al., Display, engineering, and applications of antigen-specific T cell receptors, Biomolecular Engineering, 2007, pp. 361-373, vol. 24, Elsevier B.V.

Tey, Siok-Keen, Adoptive T-cell therapy: adverse events and safety switches, Clinical & Translational Immunology, 2014, pp. 1-7, vol. 3, Australasian Society for Immunology Inc.

Smith et al., Plasticity in the Contribution of T Cell Receptor Variable Region Residues to Binding of Peptide-HLA-A2 Complexes, Journal of Molecular Biology, 2013, pp. 4496-4507, vol. 425, Elsevier Ltd.

Soto et al., MHC-class I-restricted CD4 T cells: a nanomolar affinity TCR has improved anti-tumor efficacy in vivo compared to the micromolar wild-type TCR, Cancer Immunology, Immunotherapy, 2013, pp. 359-369, vol. 62, Springer-Verlag.

Stone et al., Chapter Eight: T Cell Receptor Engineering, Methods in Enzymology, 2012, pp. 189-222, vol. 503, Elsevier Inc.

Stone et al., T-cell receptor binding affinities and kinetics: impact on T-cell activity and specificity, Immunology, 2009, pp. 165-176, vol. 126, Blackwell Publishing Ltd.

Stone et al., Role of T cell receptor affinity in the efficacy and specificity of adoptive T cell therapies, Frontiers in Immunology, Aug. 2013, pp. 1-16, vol. 4, Article 244.

Teng et al., Identification of a common docking topology with substantial variation among different TCR-peptide-MHC complexes, Current Biology, 1998, pp. 409-412, vol. 8, Current Biology Ltd.

Wang et al., On defining the rules for interactions between the T cell receptor and its ligand: A critical role for a specific amino acid residue of the T cell receptor β chain, Proceedings of the National Academy of Sciences of the United States of America, Apr. 1998, pp. 5217-5222, vol. 95, The National Academy of Sciences.

Wang et al., The structural basis of αβ T-lineage immune recognition: TCR docking topologies, mechanotransduction, and co-receptor function, Immunological Reviews, 2012, pp. 102-119, vol. 250, John Wiley & Sons A/S.

Weber et al., Class II-restricted T cell receptor engineered in vitro for higher affinity retains peptide specificity and function, Proceedings of the National Academy of Sciences, Dec. 27, 2005, pp. 19033-19038, vol. 102, No. 52, The National Academy of Sciences of the USA.

(56) References Cited

OTHER PUBLICATIONS

Zoete et al., Structure-based, rational design of T cell receptors, Frontiers in Immunology, Sep. 2013, pp. 1-19, Vo. 4, Article 268.
Patent Cooperation Treaty International Preliminary Report on Patentability (Chapter I of the Patent Cooperation Treaty) for International Application No. PCT/US2015/041625, dated Feb. 2, 2017, 12 pages, The International Bureau of WIPO.
Patent Cooperation Treaty International Search Report and Written Opinion for International Application No. PCT/US2015/041625, dated Sep. 25, 2015, 16 pages, The International Searching Authority.
Examination Report from the European Patent Office for Application No. 15824305.5 dated Feb. 8, 2019 (6 pages).
Piepenbrink, et. al., The basis for limited specificity and MHC restriction in a T cell receptor interface, Nature Communications, Jun. 5, 2013, pp. 1-9, vol. 4, Macmillan Publishers Limited.
Marrack, et. al., Evolutionarily Conserved Amino Acids That Control TCR-MHC Interaction, Annual Review of Immunology, Jan. 22, 2008, pp. 171-203, vol. 26, No. 1.
Dougan, et. al., Transnuclear TRP1-Specific CD8 T Cells with High or Low Affinity TCRs Show Equivalent Antitumor Activity, Cancer Immunology Research, Jul. 2, 2013, pp. 99-111, American Association for Cancer Research.
Pogulis, et. al., A Retroviral Vector that Directs Simultaneous Expression of Alpha and B T Cell Receptor Genes, Human Gene Therapy, Oct. 10, 1998, pp. 2299-2304, vol. 9, Mary Ann Liebert, Inc.
Blevins, et. al., How structural adaptability exists alongside HLA-A2 bias in the human [alpha][beta] TCR repertoire, Proceedings National Academy of Sciences PNAS, Feb. 16, 2016, 15 pages, vol. 113, No. 9.
Spear, et. al., Critical biological parameters modulate affinity as a determinant of function in T-cell receptor gene-modified T-cells, Cancer Immunology, Immunotherapy, Jun. 20, 2017, pp. 1411-1424, vol. 66, Springer-Verlag GmbH Germany.
Borbulevych, et. al., T cell receptors used in cancer gene therapy cross-react with MART-1/Melan-A tumor antigens via distinct mechanisms, Journal of Immunology, Sep. 1, 2011, pp. 2453-2463, vol. 187, No. 5.
Linnemann, et. al., T-Cell Receptor Gene Therapy: Critical Parameters for Clinical Success, The Journal of Investigative Dermatology, Jun. 16, 2011, pp. 1806-1816, vol. 131, No. 9.
European Search Report, dated Dec. 8, 2017, 12 pages.

\* cited by examiner

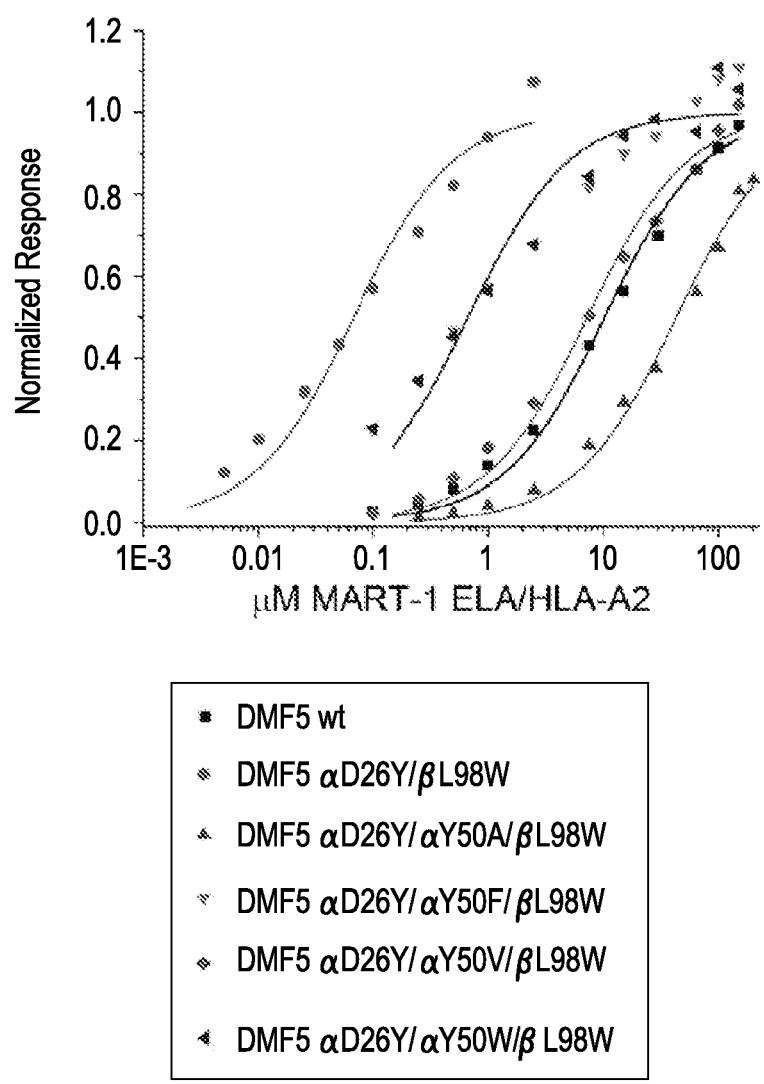

Fig. 6A

MKSLRVLLVILWLQLSWVWSQQKEVEQNSGPLSVPEGAIASLNCTYSDRGSQSFFWYRQYSGKSPELIMFIYSNGDKE
DGRFTAQLNKASQYVSLLIRDSQPSDSATYLCAVNFGGGKLIFGQGTELSVKPNIQNPDPAVYQLRDSKSSDKSVCLFTD
FDSQTNVSQSKDSDVYITDKTVLDMRSMDFKSNSAVAWSNKSDFACANAFNNSIIPEDTFFPSPESSCDVKLVEKSFETD
TNLNFQNLSVIGFRILLLKVAGFNLLMTLRLWSSTGGSGATNFSLLKQAGDVEENPGPGPRIRLLCCVAFSLLWAGPVIA
GITQAPTSQILAAGRRMTLRCTQDMRHNAMYWYRQDLGLGLRLIHYSNTAGTTGKGEVPDGYSVSRANTDDFPLTLA
SAVPSQTSVYFCASSLSFGTEAFFGQGTRLTVVEDLNKVFPPEVAVFEPSEAEISHTQKATLVCLATGFFPDHVELSWWV
NGKEVHSGVSTDPQPLKEQPALNDSRYCLSSRLRVSATFWQNPRNHFRCQVQFYGLSENDEWTQDRAKPVTQIVSAE
AWGRADCGFTSVSYQQGVLSATILYEILLGKATLYAVLVSALVLMAMVKRKDF

Fig. 6B gaagcggccgctacgtagtcgactgcacctagaatatgaaatccttgagagttttactagtgatcctgtggcttcagttgagctgggtttggagcca
acagaaggaggtggagcagaactctggaccccctcagtgttccagagggagccattgcctctctcaactgcacttacagtgaccgaggttcccagtcct
tcttctggtacagacaatattctgggaaaagccctgagttgataatgttcatatactccaatggtgacaaagaagatggaaggtttacagcacagctca
ataaagccagccagtatgtttctctgctcatcagagactcccagcccagtgattcagccacctacctctgtgccgtgaac**ttcggaggaggaaagctta
tcttcggacagggaacggagctatctgtgaaccc**aatatccagaaccctgaccctgccgtgtaccagctgagagactctaaatccagtgacaag
tctgtctgccttattcccgattttgattctcaaacaaatgtgtcacaaagtaaggattctgatgtgtatatcacagacaaaactgtgctagacatg
aggtctatggacttcaagagcaacagtgctgtggcctggagcaacaaatctgactttgcatgtgcaaacgccttcaacaacagcattattccag
aagacaccttcttccccagcccagaaagttcc**tgtgatgtcaagctggtcgagaaaagctttgaaacagatacgaacctaaacttttcaaaacctgtc
agtgattgggttccgaatcctcctcctgaaagtggccgggtttaatctgctcatgacgctgcggctgtggtccagcaccggtgggtccggagccacgaa
cttctctctgttaaagcaagcaggagacgtggaggagaacccggtcctgggccc**agaatcaggctcctgtgctgtgtggccttttctctcctgtgggc
aggtccagtgattgctgggatcacccaggcaccaacatctcagatcctggcagcaggacggcgcatgacactgagatgtacccaggatatgagacat
aatgccatgtactggtatagacaagatctaggactggggctaaggctcatccattattcaaatactgcaggtaccactggcaaaggagaagtccctga
tggttatagtgtctccagagcaaaacacagatgatttccccctcacgttggcgtctgctgtaccctctcagacatctgtgtacttctgtgccagcagtttgtc
cttcggaactgaagctttctttggacaaggcaccagactcacagttgtagaggacctgaacaaggtgttccacccgaggtcgctgtgtttgagcc
atcagaagcagagatctcccacacccaaaaggccacactggtgtgcctggccacaggcttcttccccgaccacgtggagctgagctggtgggtg
aatgggaaggaggtgcacagtggggtcagcacggacccgcagcccctcaaggagcagccgccctcaatgactccagatactgcctgagcag
ccgcctgaggtctcggccaccttctggcagaaccccgcaaccacttcgctgtcaagtccgttctacgggctctcggagaatgacgagtgga
cccaggatagggccaaaccgtcacccagatcgtcagcgccgaggccgggtagagcagac**tgtggctttacctcggtgtcctaccagcaagg
ggtcctgtctgccaccatcctctatgagatcctgctagggaaggccaccctgtatgctgtgctggtcagcgcccttgtgttgatggccatggtcaagaga
aaggatttcgaattcaaa**

SEQUENCE LISTING

<160> NUMBER OF SEQ ID NOS: 15

<210> SEQ ID NO 1
<211> LENGTH: 608
<212> TYPE: PRT
<213> ORGANISM: Homo sapiens

<400> SEQUENCE: 1

```
Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Tyr
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Phe Gly Gly Gly Lys Leu Ile Phe Gly Gln Gly Thr Glu Leu Ser
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175
```

-continued

```
Asp Lys Thr Val Leu Asp Met Arg Ser Met Asp Phe Lys Ser Asn Ser
            180                 185                 190
Ala Val Ala Trp Ser Asn Lys Ser Asp Phe Ala Cys Ala Asn Ala Phe
            195                 200                 205
Asn Asn Ser Ile Ile Pro Glu Asp Thr Phe Pro Ser Pro Glu Ser
210                 215                 220
Ser Cys Asp Val Lys Leu Val Glu Lys Ser Phe Glu Thr Asp Thr Asn
225                 230                 235                 240
Leu Asn Phe Gln Asn Leu Ser Val Ile Gly Phe Arg Ile Leu Leu Leu
                245                 250                 255
Lys Val Ala Gly Phe Asn Leu Leu Met Thr Leu Arg Leu Trp Ser Ser
            260                 265                 270
Thr Gly Gly Ser Gly Ala Thr Asn Phe Ser Leu Leu Lys Gln Ala Gly
            275                 280                 285
Asp Val Glu Glu Asn Pro Gly Pro Gly Pro Arg Ile Arg Leu Leu Cys
            290                 295                 300
Cys Val Ala Phe Ser Leu Leu Trp Ala Gly Pro Val Ile Ala Gly Ile
305                 310                 315                 320
Thr Gln Ala Pro Thr Ser Gln Ile Leu Ala Ala Gly Arg Arg Met Thr
                325                 330                 335
Leu Arg Cys Thr Gln Asp Met Arg His Asn Ala Met Tyr Trp Tyr Arg
                340                 345                 350
Gln Asp Leu Gly Leu Gly Leu Arg Leu Ile His Tyr Ser Asn Thr Ala
            355                 360                 365
Gly Thr Thr Gly Lys Gly Glu Val Pro Asp Gly Tyr Ser Val Ser Arg
            370                 375                 380
Ala Asn Thr Asp Asp Phe Pro Leu Thr Leu Ala Ser Ala Val Pro Ser
385                 390                 395                 400
Gln Thr Ser Val Tyr Phe Cys Ala Ser Ser Trp Ser Phe Gly Thr Glu
                405                 410                 415
Ala Phe Phe Gly Gln Gly Thr Arg Leu Thr Val Val Glu Asp Leu Asn
            420                 425                 430
Lys Val Phe Pro Pro Glu Val Ala Val Phe Glu Pro Ser Glu Ala Glu
            435                 440                 445
Ile Ser His Thr Gln Lys Ala Thr Leu Val Cys Leu Ala Thr Gly Phe
450                 455                 460
Phe Pro Asp His Val Glu Leu Ser Trp Trp Val Asn Gly Lys Glu Val
465                 470                 475                 480
His Ser Gly Val Ser Thr Asp Pro Gln Pro Leu Lys Glu Gln Pro Ala
                485                 490                 495
Leu Asn Asp Ser Arg Tyr Cys Leu Ser Ser Arg Leu Arg Val Ser Ala
            500                 505                 510
Thr Phe Trp Gln Asn Pro Arg Asn His Phe Arg Cys Gln Val Gln Phe
            515                 520                 525
Tyr Gly Leu Ser Glu Asn Asp Glu Trp Thr Gln Asp Arg Ala Lys Pro
            530                 535                 540
Val Thr Gln Ile Val Ser Ala Glu Ala Trp Gly Arg Ala Asp Cys Gly
545                 550                 555                 560
Phe Thr Ser Val Ser Tyr Gln Gln Gly Val Leu Ser Ala Thr Ile Leu
                565                 570                 575
Tyr Glu Ile Leu Leu Gly Lys Ala Thr Leu Tyr Ala Val Leu Val Ser
            580                 585                 590
```

```
Ala Leu Val Leu Met Ala Met Val Lys Arg Lys Asp Phe Glu Phe Lys
            595                 600                 605

<210> SEQ ID NO 2
<211> LENGTH: 608
<212> TYPE: PRT
<213> ORGANISM: Homo sapiens

<400> SEQUENCE: 2

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Tyr
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Phe Gly Gly Gly Lys Leu Ile Phe Gly Gln Gly Thr Glu Leu Ser
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

Thr Gly Gly Ser Gly Ala Thr Asn Phe Ser Leu Leu Lys Gln Ala Gly
        275                 280                 285

Asp Val Glu Glu Asn Pro Gly Pro Arg Ile Arg Leu Leu Cys
    290                 295                 300

Cys Val Ala Phe Ser Leu Leu Trp Ala Gly Pro Val Ile Ala Gly Ile
305                 310                 315                 320

Thr Gln Ala Pro Thr Ser Gln Ile Leu Ala Ala Gly Arg Arg Met Thr
                325                 330                 335

Leu Arg Cys Thr Gln Asp Met Arg His Asn Ala Met Tyr Trp Tyr Arg
            340                 345                 350

Gln Asp Leu Gly Leu Gly Leu Arg Leu Ile His Tyr Ser Asn Thr Ala
        355                 360                 365
```

Gly Thr Thr Gly Lys Gly Glu Val Pro Asp Gly Tyr Ser Val Ser Arg
        370             375             380

Ala Asn Thr Asp Asp Phe Pro Leu Thr Leu Ala Ser Ala Val Pro Ser
385             390             395             400

Gln Thr Ser Val Tyr Phe Cys Ala Ser Ser Leu Ser Phe Gly Thr Glu
            405             410             415

Ala Phe Phe Gly Gln Gly Thr Arg Leu Thr Val Val Glu Asp Leu Asn
        420             425             430

Lys Val Phe Pro Pro Glu Val Ala Val Phe Glu Pro Ser Glu Ala Glu
            435             440             445

Ile Ser His Thr Gln Lys Ala Thr Leu Val Cys Leu Ala Thr Gly Phe
        450             455             460

Phe Pro Asp His Val Glu Leu Ser Trp Trp Val Asn Gly Lys Glu Val
465             470             475             480

His Ser Gly Val Ser Thr Asp Pro Gln Pro Leu Lys Glu Gln Pro Ala
            485             490             495

Leu Asn Asp Ser Arg Tyr Cys Leu Ser Ser Arg Leu Arg Val Ser Ala
        500             505             510

Thr Phe Trp Gln Asn Pro Arg Asn His Phe Arg Cys Gln Val Gln Phe
        515             520             525

Tyr Gly Leu Ser Glu Asn Asp Glu Trp Thr Gln Asp Arg Ala Lys Pro
        530             535             540

Val Thr Gln Ile Val Ser Ala Glu Ala Trp Gly Arg Ala Asp Cys Gly
545             550             555             560

Phe Thr Ser Val Ser Tyr Gln Gln Gly Val Leu Ser Ala Thr Ile Leu
            565             570             575

Tyr Glu Ile Leu Leu Gly Lys Ala Thr Leu Tyr Ala Val Leu Val Ser
        580             585             590

Ala Leu Val Leu Met Ala Met Val Lys Arg Lys Asp Phe Glu Phe Lys
        595             600             605

<210> SEQ ID NO 3
<211> LENGTH: 608
<212> TYPE: PRT
<213> ORGANISM: Homo sapiens

<400> SEQUENCE: 3

Met Lys Ser Leu Arg Val Leu Leu Val Ile Leu Trp Leu Gln Leu Ser
1               5               10              15

Trp Val Trp Ser Gln Gln Lys Glu Val Glu Gln Asn Ser Gly Pro Leu
            20              25              30

Ser Val Pro Glu Gly Ala Ile Ala Ser Leu Asn Cys Thr Tyr Ser Asp
        35              40              45

Arg Gly Ser Gln Ser Phe Phe Trp Tyr Arg Gln Tyr Ser Gly Lys Ser
    50              55              60

Pro Glu Leu Ile Met Phe Ile Tyr Ser Asn Gly Asp Lys Glu Asp Gly
65              70              75              80

Arg Phe Thr Ala Gln Leu Asn Lys Ala Ser Gln Tyr Val Ser Leu Leu
            85              90              95

Ile Arg Asp Ser Gln Pro Ser Asp Ser Ala Thr Tyr Leu Cys Ala Val
        100             105             110

Asn Phe Gly Gly Gly Lys Leu Ile Phe Gly Gln Gly Thr Glu Leu Ser
        115             120             125

Val Lys Pro Asn Ile Gln Asn Pro Asp Pro Ala Val Tyr Gln Leu Arg

-continued

```
            130                 135                 140
Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

Thr Gly Gly Ser Gly Ala Thr Asn Phe Ser Leu Leu Lys Gln Ala Gly
        275                 280                 285

Asp Val Glu Glu Asn Pro Gly Pro Gly Pro Arg Ile Arg Leu Leu Cys
    290                 295                 300

Cys Val Ala Phe Ser Leu Leu Trp Ala Gly Pro Val Ile Ala Gly Ile
305                 310                 315                 320

Thr Gln Ala Pro Thr Ser Gln Ile Leu Ala Ala Gly Arg Arg Met Thr
                325                 330                 335

Leu Arg Cys Thr Gln Asp Met Arg His Asn Ala Met Tyr Trp Tyr Arg
            340                 345                 350

Gln Asp Leu Gly Leu Gly Leu Arg Leu Ile His Tyr Ser Asn Thr Ala
        355                 360                 365

Gly Thr Thr Gly Lys Gly Glu Val Pro Asp Gly Tyr Ser Val Ser Arg
    370                 375                 380

Ala Asn Thr Asp Asp Phe Pro Leu Thr Leu Ala Ser Ala Val Pro Ser
385                 390                 395                 400

Gln Thr Ser Val Tyr Phe Cys Ala Ser Ser Trp Ser Phe Gly Thr Glu
                405                 410                 415

Ala Phe Phe Gly Gln Gly Thr Arg Leu Thr Val Val Glu Asp Leu Asn
            420                 425                 430

Lys Val Phe Pro Pro Glu Val Ala Val Phe Glu Pro Ser Glu Ala Glu
        435                 440                 445

Ile Ser His Thr Gln Lys Ala Thr Leu Val Cys Leu Ala Thr Gly Phe
    450                 455                 460

Phe Pro Asp His Val Glu Leu Ser Trp Trp Val Asn Gly Lys Glu Val
465                 470                 475                 480

His Ser Gly Val Ser Thr Asp Pro Gln Pro Leu Lys Glu Gln Pro Ala
                485                 490                 495

Leu Asn Asp Ser Arg Tyr Cys Leu Ser Ser Arg Leu Arg Val Ser Ala
            500                 505                 510

Thr Phe Trp Gln Asn Pro Arg Asn His Phe Arg Cys Gln Val Gln Phe
        515                 520                 525

Tyr Gly Leu Ser Glu Asn Asp Glu Trp Thr Gln Asp Arg Ala Lys Pro
    530                 535                 540

Val Thr Gln Ile Val Ser Ala Glu Ala Trp Gly Arg Ala Asp Cys Gly
545                 550                 555                 560
```

-continued

Phe Thr Ser Val Ser Tyr Gln Gln Gly Val Leu Ser Ala Thr Ile Leu
            565                 570                 575

Tyr Glu Ile Leu Leu Gly Lys Ala Thr Leu Tyr Ala Val Leu Val Ser
            580                 585                 590

Ala Leu Val Leu Met Ala Met Val Lys Arg Lys Asp Phe Glu Phe Lys
            595                 600                 605

<210> SEQ ID NO 4
<211> LENGTH: 608
<212> TYPE: PRT
<213> ORGANISM: Homo sapiens

<400> SEQUENCE: 4

Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Phe Gly Gly Gly Lys Leu Ile Phe Gly Gln Gly Thr Glu Leu Ser
            115                 120                 125

Val Lys Pro Asn Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

Thr Gly Gly Ser Gly Ala Thr Asn Phe Ser Leu Leu Lys Gln Ala Gly
        275                 280                 285

Asp Val Glu Glu Asn Pro Gly Pro Gly Pro Arg Ile Arg Leu Leu Cys
    290                 295                 300

Cys Val Ala Phe Ser Leu Leu Trp Ala Gly Pro Val Ile Ala Gly Ile
305                 310                 315                 320

Thr Gln Ala Pro Thr Ser Gln Ile Leu Ala Ala Gly Arg Arg Met Thr

```
              325                 330                 335
Leu Arg Cys Thr Gln Asp Met Arg His Asn Ala Met Tyr Trp Tyr Arg
            340                 345                 350

Gln Asp Leu Gly Leu Gly Leu Arg Leu Ile His Tyr Ser Asn Thr Ala
            355                 360                 365

Gly Thr Thr Gly Lys Gly Glu Val Pro Asp Gly Tyr Ser Val Ser Arg
        370                 375                 380

Ala Asn Thr Asp Asp Phe Pro Leu Thr Leu Ala Ser Ala Val Pro Ser
385                 390                 395                 400

Gln Thr Ser Val Tyr Phe Cys Ala Ser Ser Leu Ser Phe Gly Thr Glu
                405                 410                 415

Ala Phe Phe Gly Gln Gly Thr Arg Leu Thr Val Val Glu Asp Leu Asn
            420                 425                 430

Lys Val Phe Pro Pro Glu Val Ala Val Phe Glu Pro Ser Glu Ala Glu
        435                 440                 445

Ile Ser His Thr Gln Lys Ala Thr Leu Val Cys Leu Ala Thr Gly Phe
    450                 455                 460

Phe Pro Asp His Val Glu Leu Ser Trp Trp Val Asn Gly Lys Glu Val
465                 470                 475                 480

His Ser Gly Val Ser Thr Asp Pro Gln Pro Leu Lys Glu Gln Pro Ala
                485                 490                 495

Leu Asn Asp Ser Arg Tyr Cys Leu Ser Ser Arg Leu Arg Val Ser Ala
            500                 505                 510

Thr Phe Trp Gln Asn Pro Arg Asn His Phe Arg Cys Gln Val Gln Phe
        515                 520                 525

Tyr Gly Leu Ser Glu Asn Asp Glu Trp Thr Gln Asp Arg Ala Lys Pro
    530                 535                 540

Val Thr Gln Ile Val Ser Ala Glu Ala Trp Gly Arg Ala Asp Cys Gly
545                 550                 555                 560

Phe Thr Ser Val Ser Tyr Gln Gln Gly Val Leu Ser Ala Thr Ile Leu
                565                 570                 575

Tyr Glu Ile Leu Leu Gly Lys Ala Thr Leu Tyr Ala Val Leu Val Ser
            580                 585                 590

Ala Leu Val Leu Met Ala Met Val Lys Arg Lys Asp Phe Glu Phe Lys
        595                 600                 605

<210> SEQ ID NO 5
<211> LENGTH: 9
<212> TYPE: PRT
<213> ORGANISM: Homo sapiens

<400> SEQUENCE: 5

Ala Ala Gly Ile Gly Ile Leu Thr Val
1               5

<210> SEQ ID NO 6
<211> LENGTH: 608
<212> TYPE: PRT
<213> ORGANISM: Homo sapiens

<400> SEQUENCE: 6

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Tyr
```

-continued

```
                35                  40                  45
Arg Gly Ser Gln Ser Phe Phe Trp Tyr Arg Gln Tyr Ser Gly Lys Ser
 50                  55                  60

Pro Glu Leu Ile Met Phe Ile Val Ser Asn Gly Asp Lys Glu Asp Gly
 65                  70                  75                  80

Arg Phe Thr Ala Gln Leu Asn Lys Ala Ser Gln Tyr Val Ser Leu Leu
                 85                  90                  95

Ile Arg Asp Ser Gln Pro Ser Asp Ser Ala Thr Tyr Leu Cys Ala Val
                100                 105                 110

Asn Phe Gly Gly Gly Lys Leu Ile Phe Gly Gln Gly Thr Glu Leu Ser
                115                 120                 125

Val Lys Pro Asn Ile Gln Asn Pro Asp Pro Ala Val Tyr Gln Leu Arg
                130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
                180                 185                 190

Ala Val Ala Trp Ser Asn Lys Ser Asp Phe Ala Cys Ala Asn Ala Phe
                195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
                260                 265                 270

Thr Gly Gly Ser Gly Ala Thr Asn Phe Ser Leu Leu Lys Gln Ala Gly
                275                 280                 285

Asp Val Glu Glu Asn Pro Gly Pro Gly Pro Arg Ile Arg Leu Leu Cys
                290                 295                 300

Cys Val Ala Phe Ser Leu Leu Trp Ala Gly Pro Val Ile Ala Gly Ile
305                 310                 315                 320

Thr Gln Ala Pro Thr Ser Gln Ile Leu Ala Ala Gly Arg Arg Met Thr
                325                 330                 335

Leu Arg Cys Thr Gln Asp Met Arg His Asn Ala Met Tyr Trp Tyr Arg
                340                 345                 350

Gln Asp Leu Gly Leu Gly Leu Arg Leu Ile His Tyr Ser Asn Thr Ala
                355                 360                 365

Gly Thr Thr Gly Lys Gly Glu Val Pro Asp Gly Tyr Ser Val Ser Arg
                370                 375                 380

Ala Asn Thr Asp Asp Phe Pro Leu Thr Leu Ala Ser Ala Val Pro Ser
385                 390                 395                 400

Gln Thr Ser Val Tyr Phe Cys Ala Ser Ser Leu Ser Phe Gly Thr Glu
                405                 410                 415

Ala Phe Phe Gly Gln Gly Thr Arg Leu Thr Val Val Glu Asp Leu Asn
                420                 425                 430

Lys Val Phe Pro Pro Glu Val Ala Val Phe Glu Pro Ser Glu Ala Glu
                435                 440                 445

Ile Ser His Thr Gln Lys Ala Thr Leu Val Cys Leu Ala Thr Gly Phe
                450                 455                 460
```

```
Phe Pro Asp His Val Glu Leu Ser Trp Trp Val Asn Gly Lys Glu Val
465                 470                 475                 480

His Ser Gly Val Ser Thr Asp Pro Gln Pro Leu Lys Glu Gln Pro Ala
                485                 490                 495

Leu Asn Asp Ser Arg Tyr Cys Leu Ser Ser Arg Leu Arg Val Ser Ala
            500                 505                 510

Thr Phe Trp Gln Asn Pro Arg Asn His Phe Arg Cys Gln Val Gln Phe
        515                 520                 525

Tyr Gly Leu Ser Glu Asn Asp Glu Trp Thr Gln Asp Arg Ala Lys Pro
    530                 535                 540

Val Thr Gln Ile Val Ser Ala Glu Ala Trp Gly Arg Ala Asp Cys Gly
545                 550                 555                 560

Phe Thr Ser Val Ser Tyr Gln Gln Gly Val Leu Ser Ala Thr Ile Leu
                565                 570                 575

Tyr Glu Ile Leu Leu Gly Lys Ala Thr Leu Tyr Ala Val Leu Val Ser
            580                 585                 590

Ala Leu Val Leu Met Ala Met Val Lys Arg Lys Asp Phe Glu Phe Lys
        595                 600                 605

<210> SEQ ID NO 7
<211> LENGTH: 10
<212> TYPE: PRT
<213> ORGANISM: Homo sapiens

<400> SEQUENCE: 7

Glu Leu Ala Gly Ile Gly Ile Leu Thr Val
1               5                   10

<210> SEQ ID NO 8
<211> LENGTH: 608
<212> TYPE: PRT
<213> ORGANISM: Homo sapiens

<400> SEQUENCE: 8

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Tyr
            35                  40                  45

Arg Gly Ser Gln Ser Phe Phe Trp Tyr Arg Gln Tyr Ser Gly Lys Ser
        50                  55                  60

Pro Glu Leu Ile Met Phe Ile Ala Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Phe Gly Gly Gly Lys Leu Ile Phe Gly Gln Gly Thr Glu Leu Ser
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175
```

```
Asp Lys Thr Val Leu Asp Met Arg Ser Met Asp Phe Lys Ser Asn Ser
                180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
                260                 265                 270

Thr Gly Gly Ser Gly Ala Thr Asn Phe Ser Leu Leu Lys Gln Ala Gly
                275                 280                 285

Asp Val Glu Glu Asn Pro Gly Pro Gly Pro Arg Ile Arg Leu Leu Cys
                290                 295                 300

Cys Val Ala Phe Ser Leu Leu Trp Ala Gly Pro Val Ile Ala Gly Ile
305                 310                 315                 320

Thr Gln Ala Pro Thr Ser Gln Ile Leu Ala Ala Gly Arg Arg Met Thr
                325                 330                 335

Leu Arg Cys Thr Gln Asp Met Arg His Asn Ala Met Tyr Trp Tyr Arg
                340                 345                 350

Gln Asp Leu Gly Leu Gly Leu Arg Leu Ile His Tyr Ser Asn Thr Ala
                355                 360                 365

Gly Thr Thr Gly Lys Gly Glu Val Pro Asp Gly Tyr Ser Val Ser Arg
                370                 375                 380

Ala Asn Thr Asp Asp Phe Pro Leu Thr Leu Ala Ser Ala Val Pro Ser
385                 390                 395                 400

Gln Thr Ser Val Tyr Phe Cys Ala Ser Ser Trp Ser Phe Gly Thr Glu
                405                 410                 415

Ala Phe Phe Gly Gln Gly Thr Arg Leu Thr Val Val Glu Asp Leu Asn
                420                 425                 430

Lys Val Phe Pro Pro Glu Val Ala Val Phe Glu Pro Ser Glu Ala Glu
                435                 440                 445

Ile Ser His Thr Gln Lys Ala Thr Leu Val Cys Leu Ala Thr Gly Phe
450                 455                 460

Phe Pro Asp His Val Glu Leu Ser Trp Trp Val Asn Gly Lys Glu Val
465                 470                 475                 480

His Ser Gly Val Ser Thr Asp Pro Gln Pro Leu Lys Glu Gln Pro Ala
                485                 490                 495

Leu Asn Asp Ser Arg Tyr Cys Leu Ser Ser Arg Leu Arg Val Ser Ala
                500                 505                 510

Thr Phe Trp Gln Asn Pro Arg Asn His Phe Arg Cys Gln Val Gln Phe
                515                 520                 525

Tyr Gly Leu Ser Glu Asn Asp Glu Trp Thr Gln Asp Arg Ala Lys Pro
                530                 535                 540

Val Thr Gln Ile Val Ser Ala Glu Ala Trp Gly Arg Ala Asp Cys Gly
545                 550                 555                 560

Phe Thr Ser Val Ser Tyr Gln Gln Gly Val Leu Ser Ala Thr Ile Leu
                565                 570                 575

Tyr Glu Ile Leu Leu Gly Lys Ala Thr Leu Tyr Ala Val Leu Val Ser
                580                 585                 590
```

```
Ala Leu Val Leu Met Ala Met Val Lys Arg Lys Asp Phe Glu Phe Lys
            595                 600                 605

<210> SEQ ID NO 9
<211> LENGTH: 608
<212> TYPE: PRT
<213> ORGANISM: Homo sapiens

<400> SEQUENCE: 9

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Tyr
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Val Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Phe Gly Gly Gly Lys Leu Ile Phe Gly Gln Gly Thr Glu Leu Ser
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

Thr Gly Gly Ser Gly Ala Thr Asn Phe Ser Leu Leu Lys Gln Ala Gly
        275                 280                 285

Asp Val Glu Glu Asn Pro Gly Pro Arg Ile Arg Leu Leu Cys
    290                 295                 300

Cys Val Ala Phe Ser Leu Leu Trp Ala Gly Pro Val Ile Ala Gly Ile
305                 310                 315                 320

Thr Gln Ala Pro Thr Ser Gln Ile Leu Ala Ala Gly Arg Arg Met Thr
                325                 330                 335

Leu Arg Cys Thr Gln Asp Met Arg His Asn Ala Met Tyr Trp Tyr Arg
            340                 345                 350

Gln Asp Leu Gly Leu Gly Leu Arg Leu Ile His Tyr Ser Asn Thr Ala
        355                 360                 365
```

Gly Thr Thr Gly Lys Gly Glu Val Pro Asp Gly Tyr Ser Val Ser Arg
    370                 375                 380

Ala Asn Thr Asp Asp Phe Pro Leu Thr Leu Ala Ser Ala Val Pro Ser
385                 390                 395                 400

Gln Thr Ser Val Tyr Phe Cys Ala Ser Ser Trp Ser Phe Gly Thr Glu
                405                 410                 415

Ala Phe Phe Gly Gln Gly Thr Arg Leu Thr Val Val Glu Asp Leu Asn
            420                 425                 430

Lys Val Phe Pro Pro Glu Val Ala Val Phe Glu Pro Ser Glu Ala Glu
                435                 440                 445

Ile Ser His Thr Gln Lys Ala Thr Leu Val Cys Leu Ala Thr Gly Phe
        450                 455                 460

Phe Pro Asp His Val Glu Leu Ser Trp Trp Val Asn Gly Lys Glu Val
465                 470                 475                 480

His Ser Gly Val Ser Thr Asp Pro Gln Pro Leu Lys Glu Gln Pro Ala
                485                 490                 495

Leu Asn Asp Ser Arg Tyr Cys Leu Ser Ser Arg Leu Arg Val Ser Ala
                500                 505                 510

Thr Phe Trp Gln Asn Pro Arg Asn His Phe Arg Cys Gln Val Gln Phe
        515                 520                 525

Tyr Gly Leu Ser Glu Asn Asp Glu Trp Thr Gln Asp Arg Ala Lys Pro
    530                 535                 540

Val Thr Gln Ile Val Ser Ala Glu Ala Trp Gly Arg Ala Asp Cys Gly
545                 550                 555                 560

Phe Thr Ser Val Ser Tyr Gln Gln Gly Val Leu Ser Ala Thr Ile Leu
                565                 570                 575

Tyr Glu Ile Leu Leu Gly Lys Ala Thr Leu Tyr Ala Val Leu Val Ser
            580                 585                 590

Ala Leu Val Leu Met Ala Met Val Lys Arg Lys Asp Phe Glu Phe Lys
        595                 600                 605

<210> SEQ ID NO 10
<211> LENGTH: 608
<212> TYPE: PRT
<213> ORGANISM: Homo sapiens

<400> SEQUENCE: 10

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Tyr
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Phe Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
                100                 105                 110

Asn Phe Gly Gly Gly Lys Leu Ile Phe Gly Gln Gly Thr Glu Leu Ser
            115                 120                 125

Val Lys Pro Asn Ile Gln Asn Pro Asp Pro Ala Val Tyr Gln Leu Arg

-continued

```
                130                 135                 140
Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
                180                 185                 190

Ala Val Ala Trp Ser Asn Lys Ser Asp Phe Ala Cys Ala Asn Ala Phe
                195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
                260                 265                 270

Thr Gly Gly Ser Gly Ala Thr Asn Phe Ser Leu Leu Lys Gln Ala Gly
                275                 280                 285

Asp Val Glu Glu Asn Pro Gly Pro Gly Pro Arg Ile Arg Leu Leu Cys
                290                 295                 300

Cys Val Ala Phe Ser Leu Leu Trp Ala Gly Pro Val Ile Ala Gly Ile
305                 310                 315                 320

Thr Gln Ala Pro Thr Ser Gln Ile Leu Ala Ala Gly Arg Arg Met Thr
                325                 330                 335

Leu Arg Cys Thr Gln Asp Met Arg His Asn Ala Met Tyr Trp Tyr Arg
                340                 345                 350

Gln Asp Leu Gly Leu Gly Leu Arg Leu Ile His Tyr Ser Asn Thr Ala
                355                 360                 365

Gly Thr Thr Gly Lys Gly Glu Val Pro Asp Gly Tyr Ser Val Ser Arg
                370                 375                 380

Ala Asn Thr Asp Asp Phe Pro Leu Thr Leu Ala Ser Ala Val Pro Ser
385                 390                 395                 400

Gln Thr Ser Val Tyr Phe Cys Ala Ser Ser Trp Ser Phe Gly Thr Glu
                405                 410                 415

Ala Phe Phe Gly Gln Gly Thr Arg Leu Thr Val Val Glu Asp Leu Asn
                420                 425                 430

Lys Val Phe Pro Pro Glu Val Ala Val Phe Glu Pro Ser Glu Ala Glu
                435                 440                 445

Ile Ser His Thr Gln Lys Ala Thr Leu Val Cys Leu Ala Thr Gly Phe
450                 455                 460

Phe Pro Asp His Val Glu Leu Ser Trp Trp Val Asn Gly Lys Glu Val
465                 470                 475                 480

His Ser Gly Val Ser Thr Asp Pro Gln Pro Leu Lys Glu Gln Pro Ala
                485                 490                 495

Leu Asn Asp Ser Arg Tyr Cys Leu Ser Ser Arg Leu Arg Val Ser Ala
                500                 505                 510

Thr Phe Trp Gln Asn Pro Arg Asn His Phe Arg Cys Gln Val Gln Phe
                515                 520                 525

Tyr Gly Leu Ser Glu Asn Asp Glu Trp Thr Gln Asp Arg Ala Lys Pro
                530                 535                 540

Val Thr Gln Ile Val Ser Ala Glu Ala Trp Gly Arg Ala Asp Cys Gly
545                 550                 555                 560
```

-continued

```
Phe Thr Ser Val Ser Tyr Gln Gln Gly Val Leu Ser Ala Thr Ile Leu
                565                 570                 575

Tyr Glu Ile Leu Leu Gly Lys Ala Thr Leu Tyr Ala Val Leu Val Ser
            580                 585                 590

Ala Leu Val Leu Met Ala Met Val Lys Arg Lys Asp Phe Glu Phe Lys
        595                 600                 605
```

<210> SEQ ID NO 11
<211> LENGTH: 608
<212> TYPE: PRT
<213> ORGANISM: Homo sapiens

<400> SEQUENCE: 11

```
Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Tyr
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Trp Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Phe Gly Gly Gly Lys Leu Ile Phe Gly Gln Gly Thr Glu Leu Ser
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

Thr Gly Gly Ser Gly Ala Thr Asn Phe Ser Leu Leu Lys Gln Ala Gly
        275                 280                 285

Asp Val Glu Glu Asn Pro Gly Pro Gly Pro Arg Ile Arg Leu Leu Cys
    290                 295                 300

Cys Val Ala Phe Ser Leu Leu Trp Ala Gly Pro Val Ile Ala Gly Ile
305                 310                 315                 320

Thr Gln Ala Pro Thr Ser Gln Ile Leu Ala Ala Gly Arg Arg Met Thr
```

```
                325                 330                 335
Leu Arg Cys Thr Gln Asp Met Arg His Asn Ala Met Tyr Trp Tyr Arg
            340                 345                 350
Gln Asp Leu Gly Leu Gly Leu Arg Leu Ile His Tyr Ser Asn Thr Ala
        355                 360                 365
Gly Thr Thr Gly Lys Gly Glu Val Pro Asp Gly Tyr Ser Val Ser Arg
    370                 375                 380
Ala Asn Thr Asp Asp Phe Pro Leu Thr Leu Ala Ser Ala Val Pro Ser
385                 390                 395                 400
Gln Thr Ser Val Tyr Phe Cys Ala Ser Ser Trp Ser Phe Gly Thr Glu
                405                 410                 415
Ala Phe Phe Gly Gln Gly Thr Arg Leu Thr Val Val Glu Asp Leu Asn
            420                 425                 430
Lys Val Phe Pro Pro Glu Val Ala Val Phe Glu Pro Ser Glu Ala Glu
        435                 440                 445
Ile Ser His Thr Gln Lys Ala Thr Leu Val Cys Leu Ala Thr Gly Phe
    450                 455                 460
Phe Pro Asp His Val Glu Leu Ser Trp Trp Val Asn Gly Lys Glu Val
465                 470                 475                 480
His Ser Gly Val Ser Thr Asp Pro Gln Pro Leu Lys Glu Gln Pro Ala
                485                 490                 495
Leu Asn Asp Ser Arg Tyr Cys Leu Ser Ser Arg Leu Arg Val Ser Ala
            500                 505                 510
Thr Phe Trp Gln Asn Pro Arg Asn His Phe Arg Cys Gln Val Gln Phe
        515                 520                 525
Tyr Gly Leu Ser Glu Asn Asp Glu Trp Thr Gln Asp Arg Ala Lys Pro
    530                 535                 540
Val Thr Gln Ile Val Ser Ala Glu Ala Trp Gly Arg Ala Asp Cys Gly
545                 550                 555                 560
Phe Thr Ser Val Ser Tyr Gln Gln Gly Val Leu Ser Ala Thr Ile Leu
                565                 570                 575
Tyr Glu Ile Leu Leu Gly Lys Ala Thr Leu Tyr Ala Val Leu Val Ser
            580                 585                 590
Ala Leu Val Leu Met Ala Met Val Lys Arg Lys Asp Phe Glu Phe Lys
        595                 600                 605

<210> SEQ ID NO 12
<211> LENGTH: 10
<212> TYPE: PRT
<213> ORGANISM: Homo sapiens

<400> SEQUENCE: 12

Glu Ala Ala Gly Ile Gly Ile Leu Thr Val
1               5                   10

<210> SEQ ID NO 13
<211> LENGTH: 605
<212> TYPE: PRT
<213> ORGANISM: Homo sapiens

<400> SEQUENCE: 13

Met Lys Ser Leu Arg Val Leu Leu Val Ile Leu Trp Leu Gln Leu Ser
1               5                   10                  15
Trp Val Trp Ser Gln Gln Lys Glu Val Glu Gln Asn Ser Gly Pro Leu
            20                  25                  30
Ser Val Pro Glu Gly Ala Ile Ala Ser Leu Asn Cys Thr Tyr Ser Asp
```

```
            35                  40                  45
Arg Gly Ser Gln Ser Phe Phe Trp Tyr Arg Gln Tyr Ser Gly Lys Ser
 50                  55                  60

Pro Glu Leu Ile Met Phe Ile Tyr Ser Asn Gly Asp Lys Glu Asp Gly
 65                  70                  75                  80

Arg Phe Thr Ala Gln Leu Asn Lys Ala Ser Gln Tyr Val Ser Leu Leu
                 85                  90                  95

Ile Arg Asp Ser Gln Pro Ser Asp Ser Ala Thr Tyr Leu Cys Ala Val
                100                 105                 110

Asn Phe Gly Gly Gly Lys Leu Ile Phe Gly Gln Gly Thr Glu Leu Ser
                115                 120                 125

Val Lys Pro Asn Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
                180                 185                 190

Ala Val Ala Trp Ser Asn Lys Ser Asp Phe Ala Cys Ala Asn Ala Phe
                195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
                260                 265                 270

Thr Gly Gly Ser Gly Ala Thr Asn Phe Ser Leu Leu Lys Gln Ala Gly
                275                 280                 285

Asp Val Glu Glu Asn Pro Gly Pro Gly Pro Arg Ile Arg Leu Leu Cys
                290                 295                 300

Cys Val Ala Phe Ser Leu Leu Trp Ala Gly Pro Val Ile Ala Gly Ile
305                 310                 315                 320

Thr Gln Ala Pro Thr Ser Gln Ile Leu Ala Ala Gly Arg Arg Met Thr
                325                 330                 335

Leu Arg Cys Thr Gln Asp Met Arg His Asn Ala Met Tyr Trp Tyr Arg
                340                 345                 350

Gln Asp Leu Gly Leu Gly Leu Arg Leu Ile His Tyr Ser Asn Thr Ala
                355                 360                 365

Gly Thr Thr Gly Lys Gly Glu Val Pro Asp Gly Tyr Ser Val Ser Arg
                370                 375                 380

Ala Asn Thr Asp Asp Phe Pro Leu Thr Leu Ala Ser Ala Val Pro Ser
385                 390                 395                 400

Gln Thr Ser Val Tyr Phe Cys Ala Ser Ser Leu Ser Phe Gly Thr Glu
                405                 410                 415

Ala Phe Phe Gly Gln Gly Thr Arg Leu Thr Val Val Glu Asp Leu Asn
                420                 425                 430

Lys Val Phe Pro Pro Glu Val Ala Val Phe Glu Pro Ser Glu Ala Glu
                435                 440                 445

Ile Ser His Thr Gln Lys Ala Thr Leu Val Cys Leu Ala Thr Gly Phe
                450                 455                 460
```

```
Phe Pro Asp His Val Glu Leu Ser Trp Trp Val Asn Gly Lys Glu Val
465                 470                 475                 480

His Ser Gly Val Ser Thr Asp Pro Gln Pro Leu Lys Glu Gln Pro Ala
            485                 490                 495

Leu Asn Asp Ser Arg Tyr Cys Leu Ser Ser Arg Leu Arg Val Ser Ala
        500                 505                 510

Thr Phe Trp Gln Asn Pro Arg Asn His Phe Arg Cys Gln Val Gln Phe
    515                 520                 525

Tyr Gly Leu Ser Glu Asn Asp Glu Trp Thr Gln Asp Arg Ala Lys Pro
530                 535                 540

Val Thr Gln Ile Val Ser Ala Glu Ala Trp Gly Arg Ala Asp Cys Gly
545                 550                 555                 560

Phe Thr Ser Val Ser Tyr Gln Gln Gly Val Leu Ser Ala Thr Ile Leu
                565                 570                 575

Tyr Glu Ile Leu Leu Gly Lys Ala Thr Leu Tyr Ala Val Leu Val Ser
            580                 585                 590

Ala Leu Val Leu Met Ala Met Val Lys Arg Lys Asp Phe
            595                 600                 605

<210> SEQ ID NO 14
<211> LENGTH: 1859
<212> TYPE: DNA
<213> ORGANISM: Homo sapiens

<400> SEQUENCE: 14
aaagcggccg ctacgtagtc gactgcacct agaatatgaa atccttgaga gttttactag      60
tgatcctgtg gcttcagttg agctgggttt ggagccaaca gaaggaggtg gagcagaact     120
ctggacccct cagtgttcca gagggagcca ttgcctctct caactgcact acagtgacc      180 gaggttccca gtccttcttc tggtacagac aatattctgg aaaagccct gagttgataa      240 tgttcatata ctccaatggt gacaaagaag atggaaggtt tacagcacag ctcaataaag     300
ccagccagta tgtttctctg ctcatcagag actcccagcc cagtgattca gccacctacc     360
tctgtgccgt gaacttcgga ggaggaaagc ttatcttcgg acagggaacg gagctatctg     420
tgaaacccaa tatccagaac cctgaccctg ccgtgtacca gctgagagac tctaaatcca     480
gtgacaagtc tgtctgccta ttcaccgatt ttgattctca aacaaatgtg tcacaaagta     540
aggattctga tgtgtatatc acagacaaaa ctgtgctaga catgaggtct atggacttca     600
agagcaacag tgctgtggcc tggagcaaca aatctgactt gcatgtgca aacgccttca     660 acaacagcat tattccagaa gacaccttct tccccagccc agaaagttcc tgtgatgtca     720
agctggtcga gaaaagcttt gaaacagata cgaacctaaa ctttcaaaac tgtcagtga     780 ttgggttccg aatcctcctc ctgaaagtgg ccgggtttaa tctgctcatg acgctgcggc     840
tgtggtccag caccggtggg tccggagcca cgaacttctc tctgttaaag caagcaggag     900
acgtggagga gaacccggt cctgggccca gaatcaggct cctgtgctgt gtggcctttt     960
ctctcctgtg ggcaggtcca gtgattgctg ggatcaccca ggcaccaaca tctcagatcc    1020
tggcagcagg acggcgcatg acactgagat gtacccagga tatgagacat aatgccatgt    1080
actggtatag acaagatcta ggactggggc taaggctcat ccattattca atactgcag    1140 gtaccactgg caaggagaa gtccctgatg gttatagtgt ctccagagca aacacagatg    1200
atttccccct cacgttggcg tctgctgtac cctctcagac atctgtgtac ttctgtgcca    1260
gcagtttgtc cttcggaact gaagcttct ttggacaagg caccagactc acagttgtag    1320
```

```
aggacctgaa caaggtgttc ccacccgagg tcgctgtgtt tgagccatca gaagcagaga   1380
tctcccacac ccaaaaggcc acactggtgt gcctggccac aggcttcttc cccgaccacg   1440
tggagctgag ctggtgggtg aatgggaagg aggtgcacag tggggtcagc acggacccgc   1500
agcccctcaa ggagcagccc gccctcaatg actccagata ctgcctgagc agccgcctga   1560
gggtctcggc caccttctgg cagaaccccc gcaaccactt ccgctgtcaa gtccagttct   1620
acgggctctc ggagaatgac gagtggaccc aggatagggc caaacccgtc acccagatcg   1680
tcagcgccga ggcctggggt agagcagact gtggctttac ctcggtgtcc taccagcaag   1740
gggtcctgtc tgccaccatc ctctatgaga tcctgctagg gaaggccacc ctgtatgctg   1800
tgctggtcag cgcccttgtg ttgatggcca tggtcaagag aaaggatttc gaattcaaa    1859
```

<210> SEQ ID NO 15
<211> LENGTH: 586
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (50)..(50)
<223> OTHER INFORMATION: Xaa is any amino acid except tyrosine

<400> SEQUENCE: 15

```
Lys Glu Val Glu Gln Asn Ser Gly Pro Leu Ser Val Pro Glu Gly Ala
1               5                   10                  15

Ile Ala Ser Leu Asn Cys Thr Tyr Ser Tyr Arg Gly Ser Gln Ser Phe
            20                  25                  30

Phe Trp Tyr Arg Gln Tyr Ser Gly Lys Ser Pro Glu Leu Ile Met Phe
        35                  40                  45

Ile Xaa Ser Asn Gly Asp Lys Glu Asp Gly Arg Phe Thr Ala Gln Leu
    50                  55                  60

Asn Lys Ala Ser Gln Tyr Val Ser Leu Leu Ile Arg Asp Ser Gln Pro
65                  70                  75                  80

Ser Asp Ser Ala Thr Tyr Leu Cys Ala Val Asn Phe Gly Gly Gly Lys
                85                  90                  95

Leu Ile Phe Gly Gln Gly Thr Glu Leu Ser Val Lys Pro Asn Ile Gln
            100                 105                 110

Asn Pro Asp Pro Ala Val Tyr Gln Leu Arg Asp Ser Lys Ser Ser Asp
        115                 120                 125

Lys Ser Val Cys Leu Phe Thr Asp Phe Asp Ser Gln Thr Asn Val Ser
    130                 135                 140

Gln Ser Lys Asp Ser Asp Val Tyr Ile Thr Asp Lys Thr Val Leu Asp
145                 150                 155                 160

Met Arg Ser Met Asp Phe Lys Ser Asn Ser Ala Val Ala Trp Ser Asn
                165                 170                 175

Lys Ser Asp Phe Ala Cys Ala Asn Ala Phe Asn Asn Ser Ile Ile Pro
            180                 185                 190

Glu Asp Thr Phe Phe Pro Ser Pro Glu Ser Ser Cys Asp Val Lys Leu
        195                 200                 205

Val Glu Lys Ser Phe Glu Thr Asp Thr Asn Leu Asn Phe Gln Asn Leu
    210                 215                 220

Ser Val Ile Gly Phe Arg Ile Leu Leu Leu Lys Val Ala Gly Phe Asn
225                 230                 235                 240

Leu Leu Met Thr Leu Arg Leu Trp Ser Ser Thr Gly Gly Ser Gly Ala
```

```
                    245                 250                 255
Thr Asn Phe Ser Leu Leu Lys Gln Ala Gly Asp Val Glu Glu Asn Pro
                260                 265                 270

Gly Pro Gly Pro Arg Ile Arg Leu Leu Cys Cys Val Ala Phe Ser Leu
                275                 280                 285

Leu Trp Ala Gly Pro Val Ile Ala Gly Ile Thr Gln Ala Pro Thr Ser
            290                 295                 300

Gln Ile Leu Ala Ala Gly Arg Arg Met Thr Leu Arg Cys Thr Gln Asp
305                 310                 315                 320

Met Arg His Asn Ala Met Tyr Trp Tyr Arg Gln Asp Leu Gly Leu Gly
                325                 330                 335

Leu Arg Leu Ile His Tyr Ser Asn Thr Ala Gly Thr Thr Gly Lys Gly
                340                 345                 350

Glu Val Pro Asp Gly Tyr Ser Val Ser Arg Ala Asn Thr Asp Asp Phe
                355                 360                 365

Pro Leu Thr Leu Ala Ser Ala Val Pro Ser Gln Thr Ser Val Tyr Phe
            370                 375                 380

Cys Ala Ser Ser Trp Ser Phe Gly Thr Glu Ala Phe Phe Gly Gln Gly
385                 390                 395                 400

Thr Arg Leu Thr Val Val Glu Asp Leu Asn Lys Val Phe Pro Pro Glu
                405                 410                 415

Val Ala Val Phe Glu Pro Ser Glu Ala Glu Ile Ser His Thr Gln Lys
                420                 425                 430

Ala Thr Leu Val Cys Leu Ala Thr Gly Phe Phe Pro Asp His Val Glu
            435                 440                 445

Leu Ser Trp Trp Val Asn Gly Lys Glu Val His Ser Gly Val Ser Thr
    450                 455                 460

Asp Pro Gln Pro Leu Lys Glu Gln Pro Ala Leu Asn Asp Ser Arg Tyr
465                 470                 475                 480

Cys Leu Ser Ser Arg Leu Arg Val Ser Ala Thr Phe Trp Gln Asn Pro
                485                 490                 495

Arg Asn His Phe Arg Cys Gln Val Gln Phe Tyr Gly Leu Ser Glu Asn
                500                 505                 510

Asp Glu Trp Thr Gln Asp Arg Ala Lys Pro Val Thr Gln Ile Val Ser
        515                 520                 525

Ala Glu Ala Trp Gly Arg Ala Asp Cys Gly Phe Thr Ser Val Ser Tyr
        530                 535                 540

Gln Gln Gly Val Leu Ser Ala Thr Ile Leu Tyr Glu Ile Leu Leu Gly
545                 550                 555                 560

Lys Ala Thr Leu Tyr Ala Val Leu Val Ser Ala Leu Val Leu Met Ala
                565                 570                 575

Met Val Lys Arg Lys Asp Phe Glu Phe Lys
                580                 585
```

MOLECULAR CONSTRUCTS AND USES THEREOF

CROSS-REFERENCE TO RELATED APPLICATIONS

This patent application claims the benefit of U.S. Provisional Patent Application No. 62/027,451, filed Jul. 22, 2014, which is incorporated herein in its entirety by reference.

STATEMENT REGARDING FEDERALLY SPONSORED RESEARCH OR DEVELOPMENT

This invention was made with government support under R01GM067079 and R01GM103773 awarded by the National Institutes of Health. The government has certain rights in the invention.

REFERENCE TO A SEQUENCE LISTING

The Sequence Listing associated with this application is provided in text format in lieu of a paper copy, and is hereby incorporated by reference into the specification. The name of the text file containing the Sequence Listing is "Sequence Listing_14-046_ST25.text." The text file is 6 KB, was created on Mar. 25, 2015 and is being submitted electronically via EFS-Web.

SUBMISSION OF SEQUENCE LISTING

The contents of the electronic submission of the text file Sequence Listing, which is titled Baker_SEQ_LISTING_ST25.txt, which was created on Jul. 22, 2015 and is 60 KB in size, is incorporated herein by reference in its entirety.

BACKGROUND

Field

The subject matter of the present disclosure relates to the field of molecular constructs for T-cell receptors, as well as methods of making and using these T-cell receptor molecular constructs for treating pathologies such as viral infection or cancer.

Description of Related Art

T-cell receptors (TCRs) are important elements of adaptive immunity, as they specifically recognize antigenic peptides bound to MHC proteins (peptide/MHC complexes or pMHCs) on cell surfaces. The binding of the TCRs to the antigenic peptides and the MHC proteins is responsible for initiating immune responses against the presented antigen. The TCR-pMHC interaction is notable in health and disease, especially in the areas of transplantation, autoimmunity, and as a target for therapeutics for infectious disease and cancer. Clinical trials using adoptive transfer of genetically engineered T-cells, in which tumor-specific TCRs have been transduced, have shown promise in the treatment of certain cancers such as metastatic melanoma and synovial cell sarcoma (PMID: 16946036, PMID: 19451549, PMID: 21282551).

TCRs are proteins that recognize ligands composed of two or more distinct components; characteristically this ability is referred to as dual recognition. Typically, TCRs possess only low to moderate affinity for their ligand, an antigenic peptide bound and presented by an MHC protein, also referred to as a peptide/MHC complex or pMHC. Because of the weak binding affinity of TCRs, much research has been focused on engineering TCRs with higher binding affinities to be used as therapeutics in cancer and infectious diseases (e.g., PMID: 17947658, PMID: 18997777). The aim of that research is to enhance (or equivalently, strengthen) binding affinity and thus increase the potency of the immune response. Common techniques for increasing binding affinity include in vitro evolution using yeast or phage display. While these techniques work to enhance the binding affinity of TCRs by introducing random mutations, there are concerns about maintaining the necessary specificity to the antigenic peptide and impacts from off target effects of the enhanced-affinity TCRs (PMID: 17947658, PMID: 25070852). For example, the modifications introduced into an affinity-enhanced HLA-A1-restricted MAGE-A3-specific TCR used to treat metastatic melanoma caused the death of patients due to TCR cross-recognition of an antigen from the cardiac protein, titin (PMID: 23770775).

Computational structure-guided design of T-cell receptors has been used to enhance binding affinity in a controlled fashion (e.g., PMID: 24550723, PMID: 25070852). The research, however, is still focused on modifications that enhance or strengthen binding to the pMHC. The unresolved problem that remains using these conventional approaches is the non-specific binding and cross-reactivity of the TCR, a problem which may be further enhanced with a high affinity construct. A need continues to exist in the art for development of improved artificial/synthetic T-cell receptor constructs that reduce and/or eliminate non-specific binding and cross-reactivity, while preserving at least good binding affinity and specificity towards a selected, therapeutically relevant target peptide bound by a MHC protein. Some reports define good binding affinity as that described with a $K_D$ in the low double-digit micromolar range when measured by a technique such as surface plasmon resonance.

Despite the above and other approaches, the medical arts remain in need of materials and methods for enhancing the specificity, and hence the focus, of therapeutic moieties, including cells, TCRs, anti-cancer agents, drugs, and antibodies, for improved treatment of diseases, such as viral infections and cancer.

SUMMARY

The present invention, in a general and overall sense, provides molecular constructs useful as synthetic and/or artificial, non-wild-type modified molecular constructs and dual recognition molecular constructs comprising a sequence that encodes for a TCR affinity weakening motif. Methods of using the molecular constructs in the preparation of transformed populations of cells or soluble TCR-drug and/or TCR-antibody (such as anti-CD3 antibody) conjugate moieties, that may be used in treating cancers, viral infections, and other pathologies, are also provided.

In some embodiments, the modified T-cell receptor is observed to weaken the interaction of the T-cell receptor with the major histocompatibility (MHC) protein of an MHC complex. This particular feature is described herein as a TCR affinity weakening motif. In some embodiments, the TCR affinity weakening motif is further defined as a TCR sequence having a modified TCR CDR2α region sequence, wherein tyrosine is replaced with an amino acid other than tyrosine at a position 50. For example, tyrosine may be substituted with an alanine, phenylalanine, valine or a tryptophan residue at positon 50. For example, the TCR affinity weakening motif is defined by the amino acid sequence provided at SEQ ID No. 15, wherein the "X" position amino acid can be any amino acid other than tyrosine, or other non-tyrosine moiety.

The modified T-cell receptors encoded by the molecular constructs and dual recognition molecular constructs disclosed herein, possess the advantage of increased specificity and reduced off-target recognition, and confers these properties onto a T-cell or other cell engineered to express the modified T-cell receptor encoded by any one or more of the molecular constructs or dual recognition molecular constructs provided herein.

Advantages of the present invention include reduced cross-reactivity, greater specificity of binding, and more focused molecules, cells, T-cells and other moieties useful in a variety of therapeutic applications and methods.

The following Table may be referenced in the description of the amino acid modifications (mutations) of the molecular construct and the dual recognition molecular construct provided herein that encode the modified TCR's described herein.

Amino acids, one and three letter codes

| Amino acid | Three letter code | One letter code |
|---|---|---|
| alanine | ala | A |
| arginine | arg | R |
| asparagine | asn | N |
| aspartic acid | asp | D |
| asparagine or aspartic acid | asx | B |
| cysteine | cys | C |
| glutamic acid | glu | E |
| glutamine | gln | Q |
| glutamine or glutamic acid | glx | Z |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

The following SEQ ID No's are referenced throughout the description of the present invention:
Sequence 1: Is the αD26Y/βL98W mutation (amino acid)
Sequence 2: Is the αD26Y mutation (amino acid)
Sequence 3: Is the βL98W mutation (amino acid)
Sequence 4: Is the Wild Type sequence (amino acid)
Sequence 5: Is AAG binding sequence (amino acid)
Sequence 7: Is the ELA binding sequence (amino acid)
Sequence 8: Is the αD26Y/αY50A/βL98W mutation (amino acid)
Sequence 9: Is the αD26Y/αY50V/βL98W mutation (amino acid)
Sequence 10: Is the αD26Y/αY50F/βL98W mutation (amino acid)
Sequence 11: Is the αD26Y/αY50W/βL98W mutation (amino acid)
Sequence 12: is the EEA sequence (amino acid)
Sequence 13: is the FIG. 6A Sequence (amino acid)
Sequence 14: is the FIG. 6B sequence (nucleotide)
Sequence 15: is the αY50X mutation (amino acid)

BRIEF DESCRIPTION OF THE DRAWINGS

FIG. 1A shows a ribbon diagram depicting a TCR bound to a peptide/MHC complex. The constant domains for the alpha and beta chains are shown as Cα and Cβ. The variable domains for the alpha and beta chains are shown as Vα and Vβ. The positions of the individual complementarity determining regions (CDRs) over the MHC protein are illustrated in FIG. 1B.

FIG. 4: Surface plasmon resonance experiments to determine the binding affinity of DMF5 TCRs αD26Y/αY50A/βL98W, αD26Y/αY50V/βL98W, αD26Y/αY50F/βL98W, αD26Y/αY50W/βL98W (SEQ ID NOs: 8, 9, 10, and 11) to HLA-A2 presenting the MART-1 ELA peptide (SEQ ID NO: 7). TCRs were attached to the surface of a sensor chip and increasing concentrations up to 100 micromolar of the pMHC were injected over the surface. Binding affinities were determined using a 1:1 Langmuir model.

FIG. 6A-6B. Sequences of DMF5 TCR Constructs. FIG. 6A shows an amino acid sequence that incorporates the sequences of alpha chains TRAV 12-2*01 and TRAJ23*02 and beta chains TRBV6-4*01 and TRBJ1-1*01. (Leader sequence, variable domains, joining region, constant domains, transmembrane domains, linker region). FIG. 6B shows a nucleotide sequence encoding the amino acid sequence of FIG. 6A, plus nucleotide sequence for plasmid. The functional arrangement of the sequences within the DMF5 TCR is illustrated (Leader sequence, variable domains, joining region, constant domains, transmembrane domains, linker region; added for plasmid, C119 was originally a T which created an EcoRI site).

DETAILED DESCRIPTION

Figure 1A:
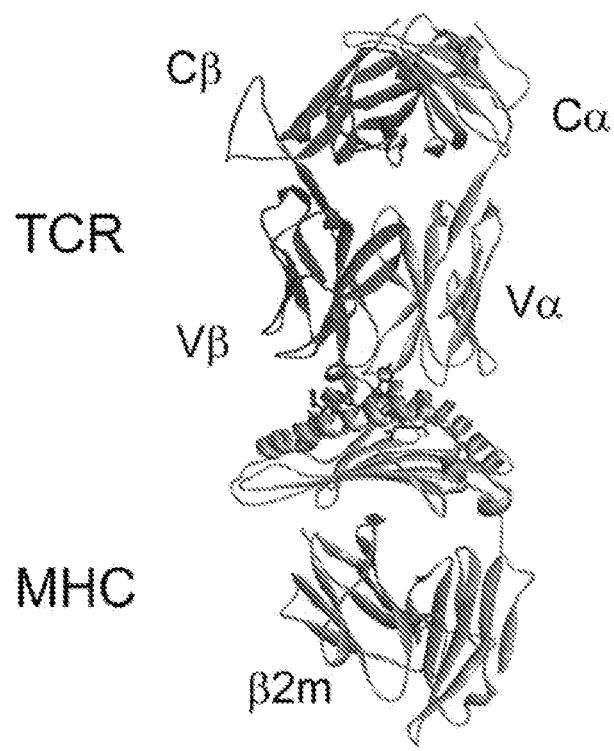
FIGS. 1A-1B.

The disclosure provides a modified T-cell receptor (TCR) comprising an amino acid sequence of a wild-type (WT) TCR with amino acid substitutions, wherein the modified TCR, as compared to the WT TCR, (i) has a reduced or weakened interaction with an MHC protein of a peptide/MHC complex and (ii) does not exhibit a decrease in antigen specificity.

As used in the description of the present invention, the term "antigen" is defined as a peptide or other molecule bound and presented by an MHC protein.

The term "wild-type" as used herein refers to a TCR which is naturally expressed by a T-cell of a host, e.g., a TCR which is endogenous to a T-cell of a host. The cells used to obtain the polynucleotides encoding the wild-type TCR are not limited to those used in Example 1. In addition, the wild-type TCR can be entirely synthesized using oligonucleotide primers corresponding to the known sequence.

The modified TCR of the disclosure is marked by one or more altered biophysical properties. In some embodiments, the modified TCR, when compared to the corresponding WT TCR, (i) has a reduced or weakened interaction with the MHC protein and (ii) does not exhibit a decrease in target antigen specificity. The term "target cells" as used herein refers to cells, which bind and present by way of an MHC protein, the target antigen which is specifically recognized by the modified TCR. The phrase "recognize the MHC protein" as used herein refers to the ability of the modified TCR to immunologically recognize (e.g., specifically bind to) an MHC protein bound to a target antigen, which may be expressed and found on the surface of a target cell. The term "reduced or weakened interaction" as used herein means that the modified TCR of the disclosure exhibits less ability to bind to the MHC protein of the target peptide/MHC complex as compared to its WT counterpart. The peptide/MHC complex could be on a target virally infected or cancer cell, dendritic cell, etc.

An MEC protein could be one of any of the classical or non-classical or non-classical class I or class II MHC proteins produced by vertebrate animals, for example as tabulated for humans in the international ImMunoGeneTics infounation system at http://www.imgt.org.

In other embodiments, the modified TCR of the disclosure exhibits the ability to recognize target pMHC without exhibiting a decrease in antigen specificity or equivalently, without displaying increased cross-reactivity, when expressed by T-cells or when used as a soluble construct. In this respect, the modified TCR is said to retain the antigen specificity of the counterpart WT TCR, e.g., recognizes the target antigen recognized by the WT TCR, is not more cross-reactive, and thus does not broadly recognize antigens that are not recognized by the WT TCR.

In other embodiments, the modified TCR of the disclosure exhibits the ability to recognize target pMHC but displays improved specificity or equivalently, less cross-reactivity when compared to the WT TCR.

A WT TCR and its counterpart modified TCR have specificity for the same antigen, which can be any antigen. The modified TCR can specifically bind to and immunologically recognize an antigen bound and presented by an MHC protein on a target cell, such that binding of the TCR elicits an immune response. Alternatively, the TCR could be a component of a soluble biologic designed to deliver a cytotoxic payload to or initiate a biological signal against a target cell. The modified TCR of the disclosure can have specificity for an antigen, which is characteristic of a disease as discussed herein, e.g., an infectious disease, an autoimmune disease, or a cancer. The antigen could be, for example, a viral antigen, a bacterial antigen, a tumor associated, a tumor specific neo-antigen, etc. The disease can be any disease involving an antigen, e.g., an infectious disease, an autoimmune disease, a cancer.

For purposes herein, "infectious disease" means a disease that can be transmitted from person to person or from organism to organism, and is caused by a microbial agent (e.g., common cold). Infectious diseases are known in the art and include, for example, hepatitis, sexually transmitted diseases (e.g., Chlamydia, gonorrhea), tuberculosis, HIV/ AIDS, diphtheria, hepatitis B, hepatitis C, cholera, and influenza.

For purposes herein, "autoimmune disease" refers to a disease in which the body produces an immunogenic (i.e., immune system) response to some constituent of its own tissue. In other words the immune system loses its ability to recognize some tissue or system within the body as "self" and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erythematosus). For example, multiple sclerosis is thought to be caused by T-cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

With respect to the methods of the disclosure, in some embodiments, the method comprises treating cancer, including acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In some embodiments, a method for treating melanoma is provided.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods of the disclosure can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

With respect to the modified TCR, the amino acid substitution(s) can be located in any part of the amino acid sequence of the TCR, but commonly located within the amino acid sequence of the complementary determining region (CDR) of the TCR alpha or beta chains, or in some cases the gamma or delta chains. These regions have been defined by elucidation of X-ray crystallographic structures, as well as sequence comparisons, which have revealed the presence of regions of high diversity encoded in germline sequences, in the case of CDR1 and CDR2 regions, as well as recombinational diversity, in the case of CDR3 region.

Five different embodiments of the amino acid substitutions in the CDRα- or β-regions are shown in SEQ ID NOS: 6, 8, 9, 10, and 11.

In some embodiments, the disclosure provides a non-native (non-wild-type), modified TCR comprising two polypeptides (i.e., polypeptide chains), such as an α chain of a TCR, a β chain of a TCR, a γ chain of a TCR, a δ chain of a TCR, or a combination thereof. The amino acid substitutions of the non-native, modified TCRs can be located in the amino acid sequence of either or both of the polypeptide chains, which constitute the TCR. In some embodiments, the amino acid substitutions are located in the amino acid sequence of the α chain of the modified TCR (selected from the group of SEQ ID NOS: 6, 8, 9, 10, and 11). In yet another embodiment, a modified soluble single chain TCR is provided. In this embodiment, the soluble single chain TCR consists of the variable domains of the T cell receptor connected by a flexible linker (Vα-linker-Vβ or Vβ-linker-Vα).

The modified TCRs of the disclosure can comprise one or more immature TCR chains comprising a leader sequence or one or more mature chains in which the leader sequence has been removed. The leader sequence of a TCR chain comprises the amino acids at the N-terminus which together serve as a signal to transport the TCR to the plasma membrane and which amino acids are removed to yield the mature form of the TCR.

The term "polypeptide" as used herein includes oligopeptides and refers to a single chain of amino acids connected by one or more peptide bonds. The polypeptide can comprise a functional portion of either or both of the α and β chains of the TCRs of the invention, such as a functional portion comprising one of more of CDR1, CDR2, and CDR3 of the variable region(s) of the α chain and/or β chain of a TCR of the disclosure.

An embodiment of the polypeptides of this disclosure can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention.

This disclosure provides compositions and methods of using the modified TCRs that enable the immunotherapy of patients with disease. Herein, "T-cells" refers to a lymphocyte matured in the thymus that plays a role in cell-mediated immunity. The disclosure provides a composition that allows modification of a subject's own T-cells (human or those of another mammal) to display modified T-cell receptors (TCRs). The uses for these modified TCRs include, but are not limited to, the treatment of cancer, viral diseases, and autoimmune diseases. The modified TCRs may also be used in cell therapies such as adoptive transfer of CD4+ T-cells, CD8+ T-cells, and/or natural killer (NK) cells to mediate a response against an antigen. The modified TCR may also be incorporated into a soluble construct, e.g., a modified TCR used to deliver a cytotoxic agent or biological signal. This disclosure provides a molecular construct comprising polynucleotides encoding a TCR as well as combinations of polynucleotides, vectors comprising these polynucleotides, and the modified T-cells produced.

"Polynucleotide" as used herein, includes "oligonucleotide," and generally means a polymer of DNA or RNA, which can be single-stranded or double stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

For the purposes of this disclosure, the polynucleotides can be comprised of natural nucleotides, modified nucleotides, analogs of nucleotides, or a mixture thereof so long as they result in the expression of a functional polypeptide in vitro. The polynucleotides can be recombinant. As used herein, the term "recombinant" refers to (i) molecules that are constructed outside living cells by joining natural or synthetic polynucleotides to polynucleotides that can replicate in a living cell, or (ii) polypeptides that result from the replication described in (i) above. For purposes herein, the replication can be in vitro replication or in vivo replication. The variants of the polypeptides produced by the polynucleotides in this disclosure produce a TCR with an interaction towards an antigen bound and presented by a MHC protein that is near to or stronger than that of an unmodified TCR and a weakened interaction or repulsion toward the MHC protein.

Figure 1B:
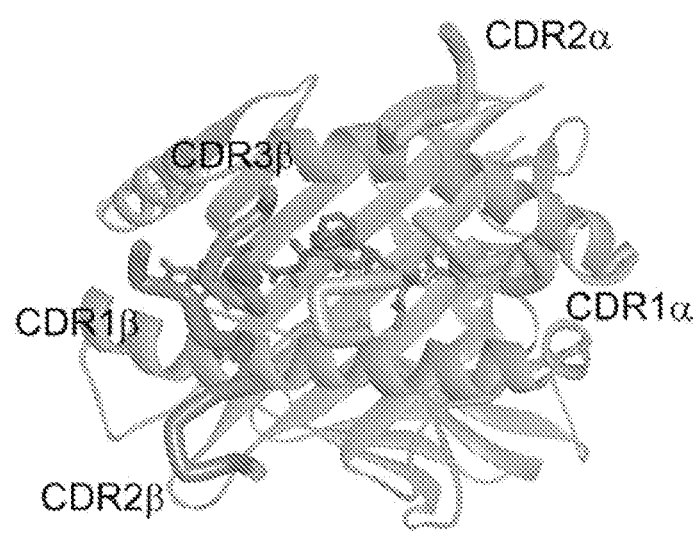

In one embodiment of this disclosure, the polynucleotides encode polypeptides that form the α- and β-chains of anti-MART-1 TCRs that are able to recognize antigens derived from the MART-1 protein a MHC class I-dependent manner MHC class I-dependent manner in one embodiment means that the TCR binds to antigens derived from the MART-1 protein bound and presented by a MHC class I molecule, wherein the MHC class I molecule is any MHC class I molecule known in the art, such as, but not limited to, HLA-A molecules. In a particular embodiment, the TCRs are able to recognize specific antigenic epitopes within the MART-1 protein, the portion of the antigen recognized by the immune system, namely, AAG (SEQ ID NO: 5), ELA (SEQ ID NO:7)), or EAA (SEQ ID NO:12, comprised of Glu-Ala-Ala-Gly-Ile-Gly-Ile-Leu-Thr-Val) bound to HLA-A2. In other embodiments, the polynucleotides encode a T-cell receptor (TCR) α-chain with a variable (V) gene segment, a joining (J) gene segment, and a constant (C) gene segment. The V segments of the polypeptide have three complementarity determining regions, the CDR1 loop, the CDR2 loop, and the CDR3 loop (FIGS. 1A-1B). In some embodiments, a residue within the CDR2 loop of the α chain that interacts with the MHC class I molecule HLA-A2 has been modified to weaken the interaction of the TCR with HLA-A2 in combination with one or more mutations designed to enhance or strengthen the interaction of the TCR with the MART-1 AAG and ELA antigens bound and presented by HLA-A2 (SEQ ID NOs: 8, 9, 10, and 11).

The polynucleotide constructs described in this disclosure can be inserted into any suitable vector. As used herein, the term "vector" refers to a polynucleotide designed for delivery to a host cell or transfer between different host cells. As used herein, a vector may be viral or non-viral. The vector may be an "expression vector" for the purpose of expressing the encoded protein in the transfected cell. Herein, a viral vector is a virus incorporating a gene to be delivered to a host cell. A non-limiting list of suitable viral vectors includes retroviral vectors, vaccinia virus vectors, adenovirus vectors, adeno associated virus (AAV) herpes virus vectors, and fowl pox virus vectors that potentially have a native or engineered capability to transduce T-cells. Useful vectors may be unencapsulated and have little or no proteins, sugars, and/or lipids surrounding them or they may be complexed with other molecules that include but are not limited to viral coats, cationic lipids, liposomes, and targeting moieties such as ligands or receptors for target cell surface molecules. Non-viral vectors include plasmids including but not limited to pCDNA3 and pGMT7.

Another aspect of this disclosure relates to a host organism into which recombinant expression vector containing all or part of the polynucleotides encoding the T-cell receptors has been introduced. The α and β chains or the γ and δ chains of the T-cells of this disclosure may be expressed independently in different hosts or in the same host. Preferably the α and β chains or the γ and δ chains are introduced into the same host to allow for formation of a functional T-cell receptor. The host cells transformed with all or part of the T-cell receptor polynucleotide sequence of this disclosure include eukaryotes, such as animal, plant, insect and yeast cells and prokaryotes, such as E. coli. By way of example animal cells may include Jurkat-cells, T-lymphocytes, peripheral blood cells, monocytes, stem cells, natural killer cells or macrophages. Suitable methods of introducing the polynucleotides into the host cells include but are not limited to electroporation, transformation, transduction, conjugation, co-transfection, co-infection, membrane fusion, liposome-cell fusion, incubation with calcium phosphate-DNA precipitate, particle bombardment mediated gene transfer, direct injection of polynucleotides encoding the T-cell receptors and direct microinjection into single cells.

The T-cells modified according to the methods of the present disclosure are usually obtained from the mammal into which the modified T-cells are likely to be transferred. These T-cells can be obtained from peripheral blood lymphocytes (PBLs) directly via an aliquot of blood or from a partially purified sample. Other sources of lymphocytes include, but are not limited to, tumor infiltrating lymphocytes (TILS), and cells from other body fluids including without limitation lymph, or lymph nodes. These modified T-cells can be transferred to a mammal for treatment or prophylaxis for disease. Methods of culturing T-cells in vitro for use in treatment are known to those skilled in the art. The dose of modified T-cells administered will vary and depend upon the pharmaceutical formulation, the method of administration, and site of administration, which will be determined by a medical professional.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

In all embodiments, the molecules can be in any stereoisomeric form, for example, enantiomers, diastereomers, tautomers and the like. In all embodiments, the fusion molecule or parts thereof includes all variants, mutations, alleles, substitutes, fragments and analogs thereof.

In some aspects, the modified molecular construct may be described as a dual recognition molecular construct. This dual recognition modified molecular construct may comprise an "affinity enhancing" motif and an "affinity weakening" motif. The "affinity enhancing" motif may be described as comprising a sequence that, when incorporated into a T cell receptor, enhances the interaction of the TCR with an antigen, peptide, or other molecule of interest. The "affinity enhancing" motif is capable of, for example, enhancing the binding of the construct, or any cell transformed to express the sequence of the affinity enhancing region, to an antigen, peptide, or other molecule of interest, such as, for example, the peptide component of a peptide MHC complex.

The "affinity weakening" motif may be described as being encoded by a sequence that, when incorporated into a T cell receptor, weakens the interaction of the TCR with a component other than the antigen, peptide, or other molecule of interest targeted by the "affinity enhancing" motif. The "affinity weakening" motif is capable of, for example, weakening the binding of the construct, or any cell transformed to express the sequence of the affinity weakening motif, to the MHC component of a peptide/MHC complex. A TCR construct that has been engineered to contain the dual recognition construct is also provided that includes both an "affinity enhancing" and an "affinity weakening" motif.

In some embodiments, the dual recognition construct may include sequences that, when incorporated into a TCR, creates an improved affinity for the target pMHC when compared to the WT (wild-type, native) TCR. In these cases, the degree of "affinity weakening" towards an MHC moiety may be less than the degree of "affinity enhancing" towards the antigen conferred by the alteration of the TCR sequence. In this case, when compared to the WT TCR, the modified TCR has a stronger Kd when measured by approaches such as surface plasmon resonance.

In some embodiments, the dual recognition construct may include sequences that, when incorporated into a TCR, creates a weaker affinity for the target pMHC when compared to the WT TCR. In these cases, the degree of "affinity weakening" towards the MHC may be greater than the degree of "affinity enhancing" towards the antigen conferred by the alteration of the TCR sequence. In this case, when compared to the WT TCR, the modified TCR has a weaker Kd when measured by approaches such as surface plasmon resonance.

In other embodiments, the molecular construct or dual recognition molecular construct includes a "affinity weakening" motif encoded by a sequence that has a TCR amino acid sequence substitution at a CDR2α chain, changing native tyrosine to phenylalanine at positon 50, thus providing for a non-native, modified TCR. However, other amino acid substitutions can be made, for example, any of the 20 common, genetically-encoded amino acids such as: tryptophan, valine, leucine, isoleucine, may be substituted for tyrosine. Other amino acids include those classified as having, for example: charged polar side chains (Arg, His, Lys, etc.); uncharged polar side chains (Thr, Asn, Gln, etc.). In addition, it is envisioned that a modified TCR according to the present invention may instead be provided by use of a molecular construct or dual recognition molecular construct that has a sequence with an addition, deletion, or other molecular modification, so as to provide a modified TCR having the properties and uses described herein.

In other embodiments, where an "affinity weakening" effect is to be imparted to the TCR, the amino acid mutations can occur at any one or more of the amino acids within the CDR2 loop of the TCR α or β chain. These mutations may be amino acid substitutions, insertions, or deletions.

In yet other embodiments, where an "affinity weakening" effect is to be imparted to a molecule, the sequence amino acid(s) to be modified (deletion, substitution, addition (insertion)) are located at a region or regions of the TCR that dock alongside the α1 or α2 helices of a class I MHC, or the α or β helices of a class II MHC protein. The particular location of a modification, therefore, may be referenced by consideration of the conformational and/or structural characteristics imparted to the three-dimensional structure of the resulting expressed molecule bound to a target pMHC.

Identification of positions to introduce "affinity weakening" mutations can be performed by examining or considering three-dimensional structures or models of three-dimensional structures of TCR-pMHC complexes. Preferably, "affinity weakening" mutations are introduced at amino acids that contact or dock alongside the α1 or α2 helices of a class I MHC protein or the α or β helices of a class II MHC protein. Examples of such positions are Tyr50 in the CDR2α loop of the DMF5 TCR (SEQ ID's 6, 8, 9, 10, 11). Possible examples for other TCRs include Tyr50 in the CDR2α loop of the A6 TCR (PMID: 8906788), Ile52 in the CDR2α loop of the B7 TCR (PMID: 9586631), Tyr49 in the CDR2α loop of the DMF4 TCR (PMID: 21795600), Tyr50 in the CDR2β loop of the DMF4 TCR.

The mutations can be introduced at the nucleic acid level or at the amino acid level. With respect to particular nucleic acid sequences, because of the degeneracy of the genetic code, a large number of functionally identical nucleic acids encode any given protein. For instance, the codons GCA, GCC, GCG and GCU all encode the amino acid alanine. Similarly, the codons GUA, GUC, GUG, and GUU all encode the amino acid valine; the codons UAC and UAU all encode the amino acid tyrosine; and the codon UGG encodes the amino acid tryptophan. Thus, at every position where an alanine is specified by a codon, the codon can be altered to any of the corresponding codons described without altering the encoded polypeptide. Such nucleic acid variations are "silent variations," which are one species of conservatively modified variations. If mutations at the nucleic acid level are introduced to encode a particular amino acid, then one or more nucleic acids are altered. For example proline is encoded by CCC, CCA, CCG, CCU; thus, one base change, e.g. CCC (proline) to GCC gives rise to alanine. Thus by way of example every natural or non-natural nucleic acid sequence herein which encodes a natural or non-natural polypeptide also describes every possible silent variation of the natural or non-natural nucleic acid. One of skill will recognize that each codon in a natural or non-natural nucleic acid (except AUG, which is ordinarily the only codon for methionine, and TGG, which is ordinarily the only codon for tryptophan) can be modified to yield a functionally identical molecule or a different molecule. Accordingly, each silent variation of a natural and non-natural nucleic acid which encodes a natural and non-natural polypeptide is implicit in each described sequence.

As to amino acid sequences, individual substitutions, deletions or additions to a nucleic acid, peptide, polypeptide, or protein sequence which alters, adds or deletes a single natural and non-natural amino acid or a small percentage of natural and non-natural amino acids in the encoded sequence, the alteration results in the deletion of an amino acid, addition of an amino acid, or substitution of a natural and non-natural amino acid with a chemically similar amino acid. Conservative substitution tables providing functionally similar natural amino acids are well known in the art. Such conservatively modified variants are in addition to and do not exclude polymorphic variants, interspecies homologs, and alleles of the methods and compositions described herein.

In another preferred embodiment, the modified molecular construct includes a non-native sequence that encodes for a peptide, protein, fragment thereof, or other molecule, that demonstrates binding affinity for a an antigen of interest. The non-native sequence may comprise one or more non-natural or analogs of amino acids.

A "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated, without user manipulation, into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

In some cases, the non-natural amino acid substitution(s) or incorporation(s) will be combined with other additions, substitutions, or deletions within the polypeptide to affect other chemical, physical, pharmacologic and/or biological traits. In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport thru tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which do not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to agonists, super-agonists, partial agonists, inverse agonists, antagonists, receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability.

For example, locations in the polypeptide required for biological activity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

The structure and activity of the non-naturally-occurring, dual recognition motif constructs that contain other modifications can be examined to determine what amino acids within the "affinity enhancing" motif and the "affinity weakening" motif are likely to be tolerant of substitution with a non-natural amino acid. Once residues that are likely to be intolerant to substitution with non-natural amino acids have been eliminated, the impact of proposed substitutions at each of the remaining positions can be examined using methods including, but not limited to, the three-dimensional structure of the relevant polypeptide, and any associated ligands or binding proteins. X-ray crystallographic and NMR structures of many polypeptides are available in the Protein Data Bank (PDB, www.rcsb.org), a centralized database containing three-dimensional structural data of large molecules of proteins and nucleic acids, one can be used to identify amino acid positions that can be substituted with non-natural amino acids. In addition, models may be made investigating the secondary and tertiary structure of polypeptides, if three-dimensional structural data is not available. Thus, the identity of amino acid positions that can be substituted with non-natural amino acids can be readily obtained. Exemplary sites of incorporation of a non-natural amino acid include, but are not limited to, those that are located within potential receptor binding regions, or regions for binding to binding proteins or ligands that may be fully or partially solvent exposed, have minimal or no hydrogen-bonding interactions with nearby residues, may be minimally exposed to nearby reactive residues, and/or may be in regions that are highly flexible as predicted by the three-dimensional crystal structure of a particular polypeptide with its associated receptor, ligand or binding proteins.

A wide variety of non-natural amino acids can be substituted for, or incorporated into, a given position in a polypeptide. By way of example, a particular non-natural amino acid may be selected for incorporation based on an examination of the three dimensional crystal structure of a polypeptide with its associated ligand, receptor and/or binding proteins, a preference for conservative substitutions

EXAMPLES

In order that the disclosure described herein may be more fully understood, the following examples are set forth. It should be understood that these examples are for illustrative purposes only and are not to be construed as limiting this invention in any manner

Example 1

Building the Molecular Constructs for Modified TCRs

Template DNA for DMF5 TCR α-chain and DMF5 TCR β-chain was inserted into separate pGMT7 vectors using NdeI and HindIII restriction sites. The DMF5 TCR was previously cloned from a melanoma patient and used in a clinical trial testing adoptive T cell transfer in melanoma (PMID: 17056587; PMID: 21795600; PMID: 19451549) and its α and β chains are comprised of the following gene segments: alpha chain TRAY 12-2*01, TRAJ23*02; beta chain TRBV6-4*01, TRBJ1-1*01. Primers for the mutation within one of the complimentarity determining regions (CDR), specifically the CDR2 loop, to enhance the interaction with the MART-1 peptide and for the mutation within the CDR2 loop to weaken the interaction with the HLA-A2 protein were created utilizing IDT Oligo Tools and Agilent Quick-Change primer design tools online (Table 1).

TABLE 1

| Chain | Modification | Binding | Sequence | SEQ. ID. NO. |
|---|---|---|---|---|
| α-chain | D26Y | MART-I | Forward: 5' GAATTGTACCTACAGTTATCGCGGTAGCCAGTC 3' | 12 |
| | | | Reverse: 5' GACTGGCTACCGCGATAACTGTAGGTACAATTC 3' | 13 |
| | Y50A | HLA-A2 | Forward: 5' GGCAAATCCCCGGAACTGATTATGTTTATTGCCTCAAACGGTGAT 3' | 14 |
| | | | Reverse: 5' ATCACCGTTTGAGGCAATAAACATAATCAGTTCCGGGGATTTGCC 3' | 15 |
| | Y50F | HLA-A2 | Forward: 5' GGCAAATCCCCGGAACTGATTATGTTTATTTTCTCAAACGGTGAT 3' | 16 |
| | | | Reverse: 5' ATCACCGTTTGAGAAAATAAACATAATCAGTTCCGGGGATTTGCC 3' | 17 |
| | Y50V | HLA-A2 | Forward: 5' GGCAAATCCCCGGAACTGATTATGTTTATTGTCTCAAACGGTGAT 3' | 18 |
| | | | Reverse: 5' ATCACCGTTTGAGACAATAAACATAATCAGTTCCGGGGATTTGCC 3' | 19 |
| | Y50W | HLA-A2 | Forward: 5' GGCAAATCCCCGGAACTGATTATGTTTATTTGGTCAAACGGTGAT 3' | 20 |
| | | | Reverse: 5' ATCACCGTTTGACCAAATAAACATAATCAGTTCCGGGGATTTGCC 3' | 21 |
| β-chain | L98W | MART-1 | Forward: 5' CTTCTGCGCATCGAGCTGGTCGTTTGGTACCGAAG 3' | 22 |
| | | | Reverse: 5' CTTCGGTACCAAACGACCAGCTCGATGCGCAGAAG 3' | 23 |

A reaction mixture containing: 125 ng of forward primer, 125 ng of reverse primer, 25-100 ng of template DNA, 12 microlitres of New England Biolabs Q5 1× Master Mix (added last), and nuclease-free water to bring the final volume to 25 microlitres was prepared. PCR was performed according to the following parameters: a) 98 C for 30 seconds, b) 98 C for 10 seconds, c) 68 C for 30 seconds, d) 68 C for 1 min/kb of plasmid DNA length, e) repeat B-D for 30 cycles, f) 72 C for 4 min, g) 10 C hold. To digest parental DNA, 1 microlitre of DpnI was added to each reaction and the samples were moved to a 37° C. water bath for 8-12 h. The samples were sequenced to confirm the identity of the molecular sequence.

Example 2

Expression and Purification of the Modified TCRs

The polypeptides encoding the modified TCR α- and β-chains, the HLA-A2 heavy chain, and β2-microglobulin (β2m) were generated in *Escherichia coli* as inclusion bodies, which were isolated and denatured in 8 M urea. TCR α- and β-chains were diluted in TCR folding buffer (50 mM Tris (pH 8), 2 mM EDTA, 2.5 M urea, 9.6 mM cysteamine, 5.5 mM cystamine, 0.2 mM PMSF) at a 1:1 ratio. HLA-A2 and β2m were diluted in MHC folding buffer (100 mM Tris (pH 8), 2 mM EDTA, 400 mM L-arginine, 6.3 mM cysteamine, 3.7 mM cystamine, 0.2 mM PMSF) at a 1:1 ratio in the presence of excess peptide. TCR and pMHC complexes were incubated for 24 h at 4° C. Afterward, complexes were desalted by dialysis at 4° C. and room temperature respectively, then purified by anion exchange followed by size-exclusion chromatography. Absorptions at 280 nm were measured spectroscopically and concentrations determined with appropriate extinction coefficients.

Example 3

Affinity Measurements for Enhanced Affinity Modified TCRs—"Affinity Enhancing" Modifications/Motifs to TCR The present example demonstrates the utility of the present invention for providing T-cell receptors having improved affinity binding properties for a target antigen. By way of example, improved binding affinity is imparted to a TCR by modification of a CDR region to include a substitution or other modification, particularly within a CDR2 region, within the α chain, β chain, or both α and β chains.

Surface plasmon resonance experiments were performed with a Biacore 3000 instrument using CM5 sensor chips. In all studies, TCR was immobilized to the sensor chip via standard amine coupling and pMHC complex was injected as an analyte. All samples were thoroughly dialyzed in HBS-EP buffer (20 mM HEPES (pH 7.4), 150 mM NaCl, 0.005% Nonidet P-20)), then degassed for at least 15 minutes prior to use. Steady-state experiments were performed with TCRs coupled onto the sensor chip at 1000-1500 response units. Injections of pMHC spanned a concentration range of 0.5-150 μM at flow rates of 5 μl/min at 25° C. Multiple data sets were globally fit using a 1:1 Langmuir binding model utilizing Bia evaluation 4.1. Kinetic titration experiments were performed with TCRs coupled at approximately 500 response units. A series of five pMHC injections, spanning 10-160 nM and 20-320 nM at 2-fold increase per titration, were flowed over TCR surfaces. Flow rates of 30 μl/min were used at 25° C. Data were fit with a 1:1 association model with drift using Bia evaluation.

Figure 2:
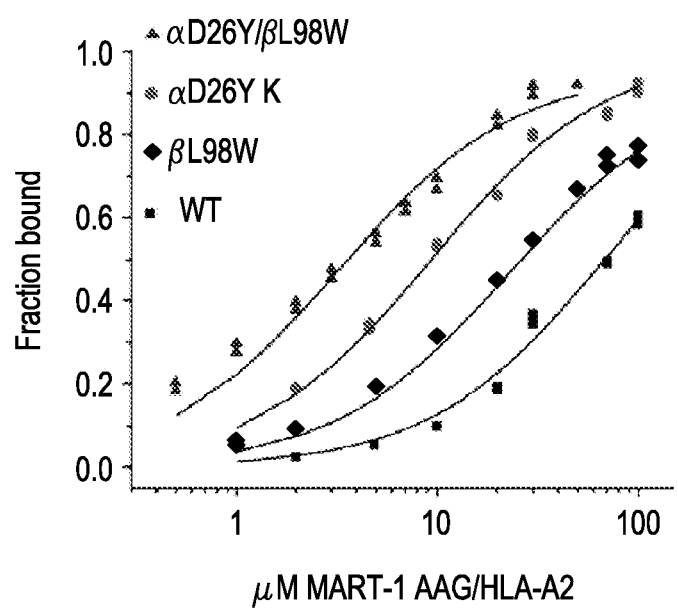
FIG. 2: Surface plasmon resonance experiments to determine the binding affinity of wild type and modified DMF5 soluble TCR constructs αD26Y/βL98W, αD26Y, βL98W, WT (SEQ ID NOs: 1, 2, 3, and 4) to HLA-A2 presenting the MART-1 AAG peptide (SEQ ID NO: 5). TCRs were attached to the surface of a sensor chip and increasing concentrations up to 100-micromolar of the pMHC complex were injected over the surface. Binding affinities were determined using a 1:1 Langmuir model.

FIG. 2 presents a graph illustrating the enhancement in affinity for a target antigen imparted to a modified TCR having a CDR1α chain mutation and/or a CDR3β chain mutation. By way of example, an affinity enhancing mutation ("affinity enhancing motif" mutation) of the modified TCR, as compared to the wild-type DMF5 TCR toward the MART-1 AAG antigen presented by the HLA-A2 protein, is imparted to the modified TCR having a CDR1α and/or a CDR3β chain mutation, and is demonstrated in the DMF5 TCR constructs αD26Y, βL98W, and αD26Y/βL98W (SEQ ID Nos 2, 3, 1, and 4 for wild type).

By way of further example, an affinity enhancing mutation ("affinity enhancing motif" mutation) of the modified TCR, as compared to the wild-type DMF5 TCR toward the MART-1 AAG antigen presented by the HLA-A2 protein, is imparted to the modified TCR having a CDR2β chain mutation, and is demonstrated in the DMF5 TCR CDR3β-chain mutation construct, L98W (CDR3β chain, position 98, leucine (L) to tryptophan (W) (SEQ ID 3).

By way of even further example, an affinity enhancing mutation ("affinity enhancing motif" mutation) of the modified TCR, as compared to the wild-type DMF5 TCR toward the MART-1 AAG antigen presented by the HLA-A2 protein, is imparted to the modified TCR having a double mutation, compared to the wild-type DMF5 TCR toward the MART-1 AAG antigen presented by the HLA-A2 protein. The double mutation TCR is demonstrated in the DMF5 TCR double mutation construct, αD26Y/βL98W, where the mutated TCR includes a CDR1α-chain mutation, αD26Y (CDR1α chain, position 26, aspartic acid (D) to tyrosine (Y) and a CDR3 β-chain mutation (CDR3β-chain, position 98, leucine (L) to tryptophan (W)) (SEQ ID 1).

The data at Table 2 and FIG. 2 demonstrates that each "affinity enhancing" mutation individually strengthens affinity, and that the double mutation has an approximate additive effect on binding affinity. Table 2 summarizes experimentally determined binding affinities for selected DMF5 mutants from FIG. 2 as well as published work (PMID: 24550723) for the two MART-1 antigens presented by HLA-A2 ("ELA"/HLA-A2; "AAG"/HLA-A2) demonstrating that the $K_D$ was enhanced for the individual mutants and that the enhancement or strengthening in the $K_D$ was approximately additive.

Example 4

Affinity Measurements for Enhanced Affinity Modified TCRs and Combination Enhanced/Weakened Affinity Modified TCRs Surface plasmon resonance experiments were performed with a Biacore 3000 instrument using CM5 sensor chips. In all studies, TCR was immobilized to the sensor chip via standard amine coupling and pMHC complex was injected as an analyte. All samples were thoroughly dialyzed in HBS-EP buffer (20 mM HEPES (pH 7.4), 150 mM NaCl, 0.005% Nonidet P-20), then degassed for at least 15 minutes prior to use. Steady-state experiments were performed with TCRs coupled onto the sensor chip at 1000-1500 response units. Injections of pMHC spanned a concentration range of 0.5-150 μM at flow rates of 5 μl/min at 25° C. Multiple data sets were globally fit using a 1:1 Langmuir binding model utilizing Biaevaluation 4.1. Kinetic titration experiments were performed with TCRs coupled at approximately 500 response units. A series of five pMHC injections, spanning 10-160 nM and 20-320 nM at 2-fold increase per titration, were flowed over TCR surfaces. Flow rates of 30 μl/min were used at 25° C. Data were fit with a 1:1 association model with drift using Biaevaluation.

Figure 3A:
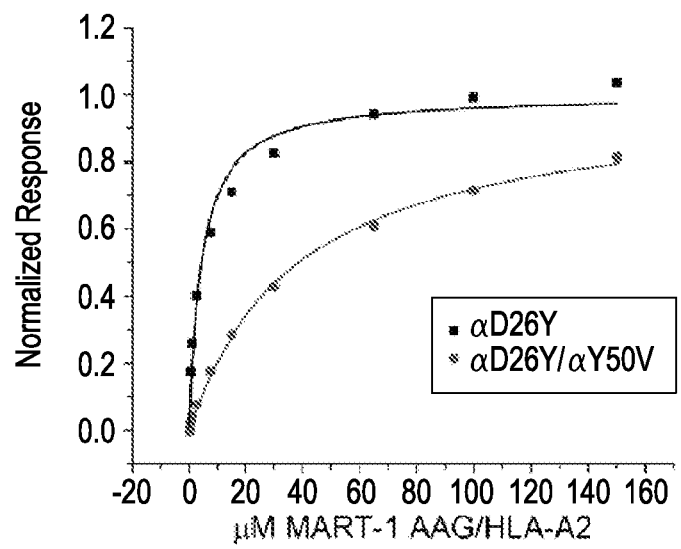
FIGS. 3A-3B: Surface plasmon resonance experiments to determine the binding affinity of modified DMF5 TCRs αD26Y, αD26Y/αY50V (SEQ OD NOs 2 and 6) to HLA-A2 presenting the MART-1 AAG peptide (FIG. 3A) (SEQ ID No. 5) or the MART-1 ELA peptide (FIG. 3B) (SEQ ID No. 7). TCRs were attached to the surface of a sensor chip and increasing concentrations up to 150 micromolar of the pMHC complex were injected over the surface. Binding affinities were determined using a 1:1 Langmuir model.
Figure 3B:
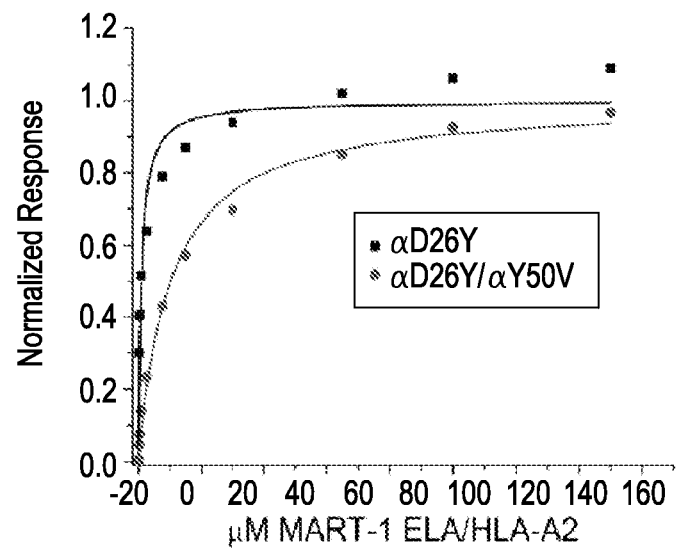
Figure 5:
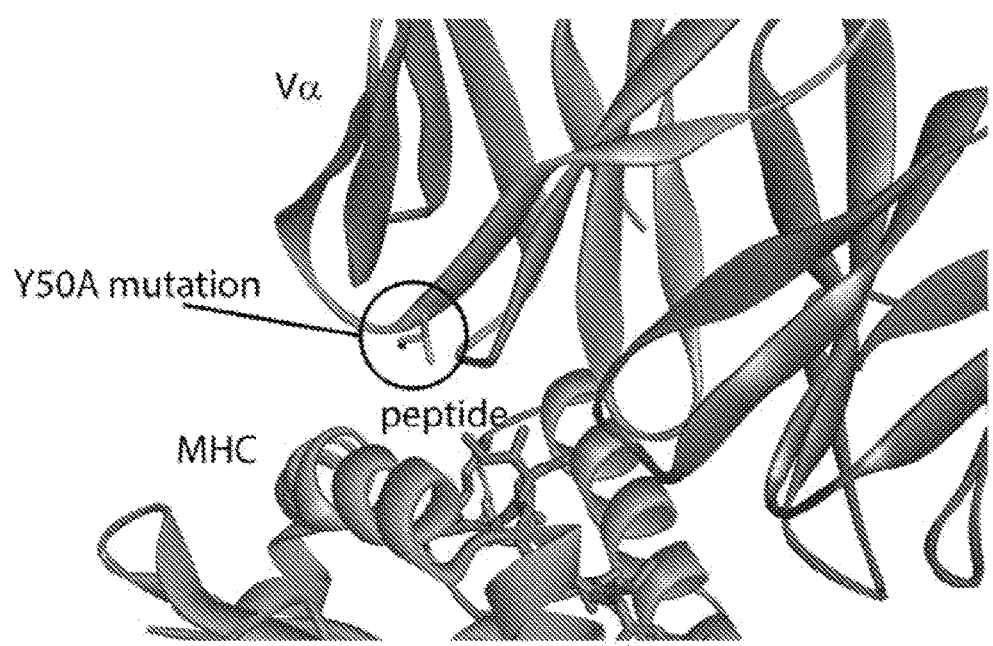
FIG. 5: Crystallographic structure of the DMF5 αD26Y/βL98W/αY50A triple mutant (SEQ ID No. 8) bound to the ELA/HLA-A2 complex. The overall structure is essentially identical to the structure of both high affinity (αD26Y/βL98W) and wild type TCRs bound to ELA/HLA-A2, with the only atoms for the Tyr50 side chain beyond the β carbon missing.

FIGS. 3A-3B shows a comparison of the binding affinities of DMF5 TCRs having double modifications comprising one mutation (TCR CDR2α chain, position 26, modification of aspartic acid (D) to tyrosine (Y)), shown to enhance the interaction between the TCR and the antigenic peptide (MART-1 epitopes AAG or ELA; SEQ ID NOs: 5 and 7) when presented by HLA-A2. A second mutation, described here as an "affinity weakening" motif, that results in a weakening of the interaction between the TCR and the human MHC class I molecule HLA-A2, was made at a TCR CDR2α chain, position 50, modification of tyrosine (Y) to valine (V). Binding was compared to DMF5 TCRs having a single mutation to enhance binding affinity (TCR CDR2α D26Y) to the antigenic peptide (MART-1 epitopes AAG or ELA; SEQ ID NOs: 5 and 7) when presented by HLA-A2. This data demonstrates that the addition of the second mutation to the DMF5 TCR to weaken the interaction (TCR CDR2αY50V) with HLA-A2 weakens the overall measured binding affinity to the pMHC complex when compared to a modified TCR with the single affinity enhancing mutation D26Y in the CDR1α loop.

TABLE 2

| DMF5 modified TCR | Target Peptide | $K_D$ (micromolar) | KD_WT/ KD_Mod | ΔΔG (kcal/mol) | SEQ ID NO |
|---|---|---|---|---|---|
| WT | ELA (SEQ ID NO 7) | 9.5 | 1 | — | 4 |
| βL98W | ELA (SEQ ID NO 7) | 2.9 | 3.3 | −0.7 | 3 |
| αD26Y | ELA (SEQ ID NO 7) | 0.46 | 20.7 | −1.8 | 2 |
| αD26Y/βL98W | AAG (SEQ ID NO 5 | 0.024 | 395.8 | −3.5 | 1 |
| WT | AAG (SEQ ID NO 5 | 43 | 1 | — | 4 |
| βL98W | MG (SEQ ID NO 5 | 11 | 3.9 | −0.8 | 3 |
| αD26Y | MG (SEQ ID NO 5 | 4.5 | 9.6 | −1.4 | 2 |
| αD26Y/βL98W | MG (SEQ ID NO 5 | 1.7 | 25.3 | −1.9 | 1 |

As shown in FIG. 4, the addition of modifications Y50A (tyrosine to alanine, position 50 of the TCR CDR2α chain), Y50V (tyrosine to valine, position 50 of the TCR CDR2α chain), Y50F (tyrosine to phenylalanine, position 50 of the TCR CDR2α chain), or Y50W (tyrosine to tryptophan, position 50 of the TCR CDR2α chain) to the DMF5 TCR CDR2α loop, that weaken the interaction between the DMF5 TCR and the MHC class I molecule HLA-A2, to modified DMF5 TCRs carrying the αD26Y/βL98W mutations that strengthen the interaction with the antigenic peptide, brings the binding affinity down to that near the wild-type DMF5 TCRs, or to less than that of wild-type DMF5 TCRs. These Y50 modifications to CDR2α moderate the very strong affinity of the αD26Y/βL98W variant DMF5 TCR (having two (2) affinity enhancing modifications). The binding affinities of the DMF5 TCRs with triple modifications shown in FIG. 4. These variants include modifications (substitutions) that weaken the interaction with the human MHC class I molecule, HLA-A2, compared to wild type DMF5 and DMF5 mutants with affinity-enhancing mutations at other positions. The DMF5 variants carrying the αD26Y/βL98W mutations are shown to strengthen the interaction with the antigenic peptide (having two (2) affinity enhancing modifications), demonstrated in Table 3.

The data in Table 4 demonstrates that an affinity weakening motif may be introduced into a TCR by mutation of the TCR CDR2α chain at an amino acid residue 50 (as calculated relative to a native TCR amino acid sequence), wherein the tyrosine is changed, and substituted with an alanine, a phenylalanine, a valine, or a tryptophan amino acid. It is anticipated that other mutations may be introduced into a CDR2α chain of a TCR at an analogous amino acid comparative conformational position, wherein the tyrosine is changed, and substituted with an alanine, a phenylalanine, a valine, or a tryptophan amino acid, to impart an affinity weakening motif, as described herein, to the TCR.

TABLE 3

| ELA | | | |
|---|---|---|---|
| | KD (micromolar) | ΔG | ΔΔG | SEQ ID NO |
| αD26Y/βL98W | 0.024 | 10.38 | — | 1 |
| αD26Y/αY50A/βL98W | 556 | 4.44 | −5.94 | 8 |
| αD26Y/αY50F/βL98W | 0.64 | 8.45 | −1.93 | 10 |
| αD26Y/αY50V/βL98W | 7.14 | 7.02 | −3.36 | 9 |
| αD26Y/αY50W/βL98W | 0.66 | 8.43 | −1.95 | 11 |

Example 5

Transfer of Polynucleotides into T-Cells

This example shows that transfer of polynucleotides encoding an α- and β-chain of a TCR into a bulk population of peripheral blood lymphocytes (PBL).

RT-PCR is performed using oligonucleotides disclosed in Example 1. The individual PCR products are inserted into the pCR2.1 vector using the TA cloning method. The β-chains are combined with the phosphoglycerol kinase promoter or an IRES. PG13 gibbon ape leukemia virus-packaging cells and the human ecotropic packaging cell line, Phoenix Eco, are co-cultured and transformed with the constructs. After co-culture, the Phoenix Eco cells are removed from the culture by negative selection with magnetic beads conjugated with anti-LYT-2 antibodies. The clones are expanded and high titer clones are selected by dot-blot titration. Southern blotting is performed to confirm vector integration and copy number.

PBL are collected by leukophoresis, and lymphocytes are separated by centrifugation on a Ficoll/Hypaque cushion, to be washed in HBSS, then are resuspended at a concentration of $1\times10^6$/ml in AIM-V medium supplemented with ng/ml OKT3, 300 IU/ml IL-2, and 5% human AB serum. The lymphocytes are cultured in vitro for 48 hours before transduction. Following stimulation, lymphocytes are transduced with retroviral vectors by transfer to culture dishes that had been precoated with retroviral vectors. To coat culture plates with vector, nontissue culture-treated six-well plates are first treated with 25 µg/ml recombinant fibronectin fragment (RetroNectin™ TM, Takara, Otsu, Japan). To these plates retroviral vector supernatant is added and the plates are incubated at 32° C., and the procedure is repeated the following day, after which time cells are expanded at 37° C. in a 5% $CO_2$ incubator and split as necessary to maintain cell density between $0.5\times10^6$ cells/ml and $4\times10^6$ cells/ml.

Example 6

Method of Treating Disease in a Host Using Modified TCRs

PBLs are obtained by leukophoresis from a metastatic melanoma patient who is HLA-A*0201 positive. The PBLs are transduced with polynucleotides encoding a WT alpha chain and a modified beta chain of a TCR specific for a tumor-specific or tumor-associated antigen. An example might be the tumor associated MART-1 AAG antigen described herein. The patient receives the transduced cells at the time of maximum lympho depletion. One month post-adoptive cell transfer, quantitative RT-PCR assays are carried out to reveal whether the presence of the modified TCRs resulted in expression by cells of the patient. Tumor regression is also analyzed by the methods described in (PMID: 16946036).

It is anticipated that the modified TCRs of the present invention may be modified to include any number of therapeutic agents. The therapeutic agents which may be associated with the TCRs of the invention include, but are not limited to, radioactive compounds, prodrug activating enzymes (DT-diaphorase (DTD) or Biphenyl hydrolase-like protein (BPHL) for example), chemotherapeutic agents (cis-platin for example), toxins (Pseudomonas exotoxin such as PE38, calcimycin or diphtheria toxin for example), immune-modulating antibody fragments such as anti-CD3 or anti-CD16 for example, or immune-modulating cytokines (IL-2 for example). To ensure that toxic effects are exercised in the desired location the toxin could be inside a liposome linked to TCR so that the compound is released slowly or through coupling the toxin to the TCR via a labile linker. This will prevent damaging effects during the transport in the body and ensure that the toxin has maximum effect after binding of the TCR to the relevant antigen presenting cells.

Other suitable therapeutic agents include but are not limited to: small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin; peptide cytotoxins, i.e. proteins or fragments thereof with the ability to kill mammalian cells. For example, ricin, diphtheria toxin, pseudomonas bacterial exotoxin A, DNase and RNase; radio-nuclides, i.e. unstable isotopes of elements which decay with the concurrent emission of one or more of alpha or beta particles, or gamma rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof; immuno-stimulants, i.e. immune effector molecules which stimulate immune response. For example, cytokines such as IL-2 and IFN-gamma, Superantigens and mutants thereof; TCR-HLA fusions, wherein the HLA defines an immunogenic antigen; chemokines such as IL-8, platelet factor 4, melanoma growth stimulatory protein, etc.; antibodies or fragments thereof, including anti-T cell or NK-cell determinant antibodies (e.g. anti-CD3 or anti-CD28 or anti-CD16); complement activators; xenogeneic protein domains, allogeneic protein domains, viral/bacterial protein domains, viral/bacterial peptides.

Example 7

Soluble Molecular Constructs for Modified TCRs

An additional embodiment of the claimed invention is for soluble molecular constructs of the modified T-cell receptors. Soluble molecular constructs are those not incorporated or embedded in a cell membrane and soluble in aqueous solutions under physiological conditions.

Typically, soluble TCRs are generated by deleting or excluding the membrane spanning helices of the alpha and beta chains or gamma and delta chains. By way of example, constructs of soluble TCRs are provided here at Examples 1 and 2. Examples 1 and 2 show the making of molecular constructs for soluble TCRs, while Examples 3 and 4 illustrate the weakening of the interaction between the soluble DMF5 TCR and the MHC class I molecule, HLA-A2 (TCR affinity weakening motif) and the strengthening of the interaction of the soluble DMF5 TCR with antigenic peptides (TCR affinity enhancing motif).

These soluble constructs may be genetically or chemically attached to another moiety, e.g., such as a therapeutic molecule, cytotoxic molecule, drug or antibody. In this fashion, the modified TCR could be used therapeutically to deliver a cytotoxic agent to a targeted cell or carry another protein capable of initiating a biologic response against a cell with a targeted pMHC, and would be referred to as a TCR-based pharmaceutical. By virtue of their soluble character, such pharmaceuticals could be delivered therapeutically similar to the manner in which current antibody-based pharmaceuticals are delivered. These pharmaceuticals would provide an improvement over current soluble TCR-based pharmaceuticals in that, among other things, they would possess improved antigen specificity and decreased cross-reactivity, compared to preparations without the TCR affinity weakening motif as described in the present invention.

Example 8

Molecular Constructs in Cancer Therapeutics

There are known to be tumor-associated and tumor-specific antigens. An additional embodiment of the claimed invention provides for using the modified TCRs as the foundation of pharmaceutical treatments useful for treating a variety of cancers.

The present example demonstrates the utility of the present invention for use in the formulation and as components of therapeutics for melanoma and other cancers. For administration to patients, the modified TCRs of the invention, T cells transformed with modified TCRs of the invention, or conjugates to the modified TCRs with one or more anti-cancer drugs, may be provided in a pharmaceutical composition together with a pharmaceutically acceptable carrier, and administered provided to a patient. In this manner, a pharmaceutical composition comprising a plurality of cells presenting the modified TCRs of the present invention (especially those TCR modifications imparting an "affinity weakening" motif, such as substitution of TCR CDR2α Y50A, F, V or W), may be combined with a pharmaceutically acceptable carrier may be provided.

For example, one therapeutic preparation for cancer may be provided with a conjugate molecule comprising one or more of the present modified TCRs (comprising an "affinity weakening" motif modification) and an anti-cancer agent, such as an anti-CD3 antibody, wherein the anti-CD3 antibody is covalently linked to the C or N terminus of the modified TCR CDR2α or β chain.

Therapeutic or imaging TCRs, multivalent TCR complexes and cells in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, preferably a parenteral (including subcutaneous, intramuscular, or preferably intravenous) route. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

Soluble forms of the modified TCRs of the invention may be associated (covalently or otherwise) with a detectable label (for diagnostic purposes wherein the TCR is used to detect the presence of particular types of cells; a therapeutic agent; a PK modifying moiety (for example by PEGylation); or a combination of the above.

Detectable labels for diagnostic purposes include, but are not limited to, fluorescent or luminescent labels, radiolabels, MRI or CT contrast reagents, or enzymes that produce a detectable product.

Therapeutic agents which may be associated with the TCRs of the invention include, but are not limited to, radioactive compounds, prodrug activating enzymes (DT-diaphorase (DTD) or Biphenyl hydrolase-like protein (BPHL) for example), chemotherapeutic agents (cis-platin for example), toxins (Pseudomonas exotoxin such as PE38, calcimycin or diphtheria toxin for example), immune-modulating antibody fragments such as anti-CD3 or anti-CD16 for example, or immune-modulating cytokines (IL-2 for example). To ensure that toxic effects are exercised in the desired location the toxin could be inside a liposome linked to TCR so that the compound is released slowly or through coupling the toxin to the TCR via a labile linker. This will prevent damaging effects during the transport in the body and ensure that the toxin has maximum effect after binding of the TCR to the relevant antigen presenting cells.

Other suitable therapeutic agents include but are not limited to: small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin; peptide cytotoxins, i.e. proteins or fragments thereof with the ability to kill mammalian cells. For example, ricin, diphtheria toxin, pseudomonas bacterial exotoxin A, DNase and RNase; radio-nuclides, i.e. unstable isotopes of elements which decay with the concurrent emission of one or more of .alpha. or .beta. particles, or .gamma. rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof; immuno-stimulants, i.e. immune effector molecules which stimulate immune response. For example, cytokines such as IL-2 and IFN-γ, Superantigens and mutants thereof; TCR-HLA fusions, wherein the HLA defines an immunogenic antigen; chemokines such as IL-8, platelet factor 4, melanoma growth stimulatory protein, etc; antibodies or fragments thereof, including anti-T cell or NK-cell determinant antibodies (e.g. anti-CD3 or anti-CD28 or anti-CD16); complement activators; xenogeneic protein domains, allogeneic protein domains, viral/bacterial protein domains, viral/bacterial peptides.

One preferred embodiment is provided by a TCR of the invention associated with an anti-CD3 antibody, or a functional fragment or variant of said anti-CD3 antibody. Antibody fragments and variants/analogues which are suitable for use in the compositions and methods described herein include but are not limited to minibodies, Fab fragments, $F(ab')_2$ fragments, dsFv and scFv fragments, or other antibody scaffold proteins such as Nanobodies™ (these constructs, marketed by Ablynx (Belgium), comprise synthetic single immunoglobulin variable heavy domain derived from a camelid (e.g. camel or llama) antibody), Domain Antibodies (marketed by Domantis (Belgium), comprising an affinity matured single immunoglobulin variable heavy domain or immunoglobulin variable light domain), UniBodies (marketed by Genmab, UniBodies are modified fully human IgG4 antibodies where the hinge region of the antibody has been eliminated), Trifunctional Antibodies (monoclonal antibodies with binding sites for two different antigens), Affibodies (marketed by Affibody, Affibodies are based on a 58-amino acid residue protein domain, a three helix bundle domain, derived from one of the IgG-binding domains of staphylococcal protein A), Anticalins (antibody mimetics synthesised from human lipocalins, which can also be formatted as dual targeting proteins, so-called Duocalins) or DARPins (Designed Ankyrin Repeat Proteins) (which are another example of antibody mimetic based on repeat proteins, such as ankyrin or leucine-rich repeat proteins, which are ubiquitous binding molecules).

All references, including publications, patent applications, and patents, cited herein are hereby incorporated by reference to the same extent as if each reference were individually and specifically indicated to be incorporated by reference and were set forth in its entirety herein.

All patents, patent applications, and scientific publications mentioned herein above are incorporated by reference into this application in their entirety.

BIBLIOGRAPHY

1. U.S. Pat. No. 4,873,190
2. U.S. Pat. No. 4,874,845
3. U.S. Pat. No. 4,946,778
4. U.S. Pat. No. 4,970,296
5. U.S. Pat. No. 5,223,409
6. U.S. Pat. No. 5,258,498
7. U.S. Pat. No. 5,260,203
8. U.S. Pat. No. 5,580,961
9. U.S. Pat. No. 5,614,192
10. U.S. Pat. No. 5,733,743
11. U.S. Pat. No. 5,780,225
12. U.S. Pat. No. 5,789,208
13. U.S. Pat. No. 5,830,755
14. U.S. Pat. No. 5,837,477
15. U.S. Pat. No. 5,840,304
16. U.S. Pat. No. 5,882,945
17. U.S. Pat. No. 5,977,321
18. U.S. Pat. No. 6,140,120
19. U.S. Pat. No. 6,165,787
20. U.S. Pat. No. 6,270,772
21. U.S. Pat. No. 6,300,065
22. U.S. Pat. No. 6,319,713
23. U.S. Pat. No. 6,416,971
24. U.S. Pat. No. 6,423,538
25. U.S. Pat. No. 6,682,736
26. U.S. Pat. No. 6,696,251
27. U.S. Pat. No. 6,699,658
28. U.S. Pat. No. 6,759,243
29. U.S. Pat. No. 6,805,861
30. U.S. Pat. No. 6,815,171
31. U.S. Pat. No. 6,838,290
32. U.S. Pat. No. 6,864,359
33. U.S. Pat. No. 6,951,917
34. U.S. Pat. No. 6,972,193
35. U.S. Pat. No. 7,109,003
36. U.S. Pat. No. 7,115,361
37. U.S. Pat. No. 7,166,707
38. U.S. Pat. No. 7,169,905
39. U.S. Pat. No. 7,186,810
40. U.S. Pat. No. 7,189,827
41. U.S. Pat. No. 7,261,894
42. U.S. Pat. No. 7,265,218
43. U.S. Pat. No. 7,329,731
44. U.S. Pat. No. 7,355,008
45. U.S. Pat. No. 7,465,787
46. U.S. Pat. No. 7,501,501
47. U.S. Pat. No. 7,557,190
48. U.S. Pat. No. 7,569,357
49. U.S. Pat. No. 7,576,183
50. U.S. Pat. No. 7,608,410
51. U.S. Pat. No. 7,632,497
52. U.S. Pat. No. 7,871,817

53. U.S. Pat. No. 7,894,995
54. U.S. Pat. No. 7,915,036
55. U.S. Pat. No. 7,960,512
56. U.S. Pat. No. 8,088,379
57. U.S. Pat. No. 8,143,376
58. U.S. Pat. No. 8,143,379
59. U.S. Pat. No. 8,192,737
60. U.S. Pat. No. 8,193,321
61. U.S. Pat. No. 8,216,574
62. U.S. Pat. No. 8,217,147
63. U.S. Pat. No. 8,293,237
64. U.S. Pat. No. 8,372,636
65. U.S. Pat. No. 8,378,074
66. U.S. Pat. No. 8,383,364
67. U.S. Pat. No. 8,383,401
68. U.S. Pat. No. 8,409,577
69. U.S. Pat. No. 8,461,306
70. U.S. Pat. No. 8,491,895
71. U.S. Pat. No. 8,491,913
72. U.S. Pat. No. 8,530,627
73. U.S. Pat. No. 8,552,150
74. U.S. Pat. No. 8,586,714
75. U.S. Pat. No. 8,617,845
76. U.S. Pat. No. 8,652,466
77. U.S. Pat. No. 8,691,730
78. U.S. Pat. No. 8,697,071
79. U.S. Pat. No. 8,716,450
80. U.S. Pat. No. 8,722,855
81. U.S. Pat. No. 8,735,546
82. U.S. Pat. No. 8,741,860
83. U.S. Pat. No. 8,784,808
84. U.S. Pat. No. 8,784,823
85. U.S. Pat. No. 8,785,599
86. U.S. Pat. No. 8,785,601
87. U.S. Pat. No. 8,802,093
88. U.S. Pat. No. 8,822,645
89. US Pub 2002/0058253
90. US Pub 2002/0165149
91. US Pub 2002/0172979
92. US Pub 2002/0176864
93. US Pub 2003/0007978
94. US Pub 2003/0036506
95. US Pub 2003/0036644
96. US Pub 2004/0146952
97. US Pub 2004/0146976
98. US Pub 2005/0064526
99. US Pub 2005/0074853
100. US Pub 2005/0136402
101. US Pub 2005/0249723
102. US Pub 2005/0260222
103. US Pub 2006/0166314
104. US Pub 2006/0240033
105. US Pub 2006/0275282
106. US Pub 2007/0055049
107. US Pub 2007/0134261
108. US Pub 2007/0190533
109. US Pub 2007/0192036
110. US Pub 2007/0192037
111. US Pub 2007/0202591
112. US Pub 2008/0009519
113. US Pub 2008/0064859
114. US Pub 2008/0213237
115. US Pub 2008/0260762
116. US Pub 2008/0267987
117. US Pub 2008/0299137
118. US Pub 2009/0053184
119. US Pub 2009/0068226
120. US Pub 2009/0175867
121. US Pub 2009/0217403
122. US Pub 2009/0275137
123. US Pub 2009/0280135
124. US Pub 2009/0280560
125. US Pub 2010/0009863
126. US Pub 2010/0021468
127. US Pub 2010/0034834
128. US Pub 2010/0093979
129. US Pub 2010/0158881
130. US Pub 2010/0297093
131. US Pub 2011/0008382
132. US Pub 2011/0034532
133. US Pub 2011/0217308
134. US Pub 2011/0243995
135. US Pub 2011/0262479
136. US Pub 2012/0015888
137. US Pub 2012/0071420
138. US Pub 2012/0148601
139. US Pub 2012/0207673
140. US Pub 2012/0252742
141. US Pub 2013/0089541
142. US Pub 2013/0178605
143. US Pub 2013/0195900
144. US Pub 2013/0274203
145. US Pub 2013/0280220
146. US Pub 2013/0330335
147. US Pub 2013/0336977
148. US Pub 2014/0031292
149. US Pub 2014/0056936
150. US Pub 2014/0066599
151. US Pub 2014/0120622
152. US Pub 2014/0154250
153. US Pub 2014/0154252
154. US Pub 2014/0187753
155. US Pub 2014/0206620
156. US Pub 2014/0234218
157. US Pub 2014/0335053
158. US Pub 2014/0371085
159. US Pub 2014/0349855
160. US Pub 2014/0099699
161. US Pub 2013/0189309
162. US Pub 2013/0149289
163. US Pub 2012/0190828
164. US Pub 2012/0071420
165. US Pub 2012/0027739
166. US Pub 2011/0262414
167. US Pub 2011/0014169
168. US Pub 2010/0166722
169. US Pub 2010/0113300
170. Baker B M et al., (2012), Immunol Rev., vol. 250(1): 10-31.
171. Bhati M et al., (2014), Protein Sci., vol. 23(3):260-72.
172. Borg N A et al., (2005), Nat Immunol., vol. 6(2):171-80.
173. Bowerman N A et al., (2009), J Biol Chem., vol. 284(47):32551-61.
174. Bowerman N A et al., (2009), Mol Immunol., vol. 46(15):3000-8.
175. Brophy S E et al., (2003), J Immunol Methods, vol. 272(1-2):235-46.
176. Chervin A S et al., (2013), Gene Ther., vol. 20(6):634-44.
177. Chervin A S et al., (2008), J Immunol Methods. vol. 339(2):175-84.
178. Chlewicki L K et al., (2005), J Mol Biol., vol. 346(1): 223-39.

179. Cho S et al., (2005), Structure, vol. 13(12):1775-87.
180. Cole D K et al., (2014), J Biol Chem., vol. 289(2): 628-38.
181. de Haan E C et al., (2001), Biologicals, vol. 29(3-4): 289-92.
182. Dunn S M et al., (2006), Protein Sci., vol. 15(4):710-21.
183. Goyarts E C et al., (1998), Mol Immunol., vol. 35(10): 593-607.
184. Haidar J N et al., (2009), Proteins, vol. 74:948-960.
185. Haidar J N et al., (2009), Proteins, vol. 74(4):948-60.
186. Holler P D et al., (2003), Nat Immunol., vol. 4(1):55-62.
187. Holler P D et al., (2000), Proc Natl Acad Sci USA, vol. 97(10):5387-92.
188. Holler & Kranz, (2004), Mol Immunol., vol. 40(14-15):1027-31.
189. Jones L L et al., (2008), J Immunol., vol. 181(9):6255-64.
190. Kranz D M., (2005), Nat Immunol., vol. 6(2):130-2.
191. Lazoura E et al., (2009), Mol Immunol. vol. 46(6): 1171-8.
192. Lefranc M P et al., (1999), Nucleic Acids Res., vol. 27(1):209-12.
193. Lynch J N et al., (2013), Mol Immunol. vol. 53(3): 283-94.
194. Manning T C et al., (1998), Immunity, vol. 8(4):413-25.
195. McBeth C et al. (2008), J Mol Biol., vol. 375(5):1306-19.
196. Morgan R A et al., (2006), Science, vol. 314(5796): 126-129.
197. Pierce B G et al., (2010), Biochemistry, vol. 49(33): 7050-9.
198. Pierce B G et al., (2014), PLoS Comput Biol., vol. 10(2):e1003478.
199. Richman S A et al., (2006), Protein Eng Des Sel., vol. 19(6):255-64.
200. Richman & Kranz, (2007), Biomol Eng. Vol. 24(4): 361-73.
201. Siok-Keen Tey, (2014), Clinical & Translational Immunology, vol. 3, e17
202. Smith S N et al., (2013), J Mol Biol., vol. 425(22): 4496-507.
203. Soto C M et al., (2013), Cancer Immunol Immunother, vol. 62(2):359-69.
204. Stone J D et al., (2012), Methods Enzymol., vol. 503:189-222.
205. Stone J D et al., (2009), Immunology, vol. 126(2):165-76.
206. Stone & Kranz, (2013), Front Immunol., vol. 4:244.
207. Teng M K et al., (1998), Curr Biol., vol. 8(7):409-12.
208. Wang F et al., (1998), Proc Natl Acad Sci USA., vol. 95(9):5217-22.
209. Wang & Reinherz, (2012), Immunol Rev., vol. 250(1): 102-19.
210. Weber K S et al., (2005), Proc Natl Acad Sci USA, vol. 102(52):19033-8.
211. Zoete V et al., (2013), Front Immunol., vol. 4:268.

What is claimed is:

1. A modified dual recognition DMF5 T-cell receptor (TCR), wherein the CDR2α chain of the TCR has a D26Y mutation, the CDR2β chain of the TCR has a L98W mutation, and the amino acid residue at position 50 of the CDR2α chain is a residue other than tyrosine.

2. The TCR of claim 1 wherein the residue at position 50 of the CDR2α chain is alanine, phenylalanine, valine or tryptophan.

3. The TCR of claim 1 wherein the CDR2α chain comprises the amino acid sequence of SEQ ID No. 15, where X is an amino acid residue other than tyrosine.

4. The TCR of claim 2 wherein the CDR2α chain comprises the amino acid sequence of SEQ ID No. 15, where X is alanine, phenylalanine, valine or tryptophan.

5. A polynucleotide encoding the engineered TCR of claim 1.

6. A polynucleotide encoding the amino acid sequence of SEQ ID No. 15, wherein X is an amino acid residue other than tyrosine.

7. A polynucleotide encoding the amino acid sequence of SEQ ID No. 15, wherein X is alanine, phenylalanine, valine or tryptophan.

8. A vector comprising the polynucleotide of claim 1.

9. The vector of claim 8, wherein the vector is a viral vector.

10. The vector of claim 9, wherein the viral vector is selected from the group consisting of retroviral vectors, vaccinia virus vectors, adenovirus vectors, adeno associated virus (AAV) herpes virus vectors, and fowl pox virus vectors.

11. The vector of claim 8, wherein the vector is a non-viral vector.

12. The vector of claim 11, wherein the non-viral vector is a plasmid.

13. A pharmaceutical composition comprising a pharmaceutically acceptable carrier and a TCR-therapeutic agent conjugate, wherein said therapeutic agent is covalently linked to a C or N-terminal of a TCR as claimed in claim 1.

14. The composition of claim 13, wherein the composition is for use in the treatment of a disease in an animal.

15. The composition of claim 13, wherein the composition is for use in the treatment of cancer.

16. The composition of claim 15, wherein the composition further comprises an anti-cancer agent.

17. The composition of claim 16, wherein the anti-cancer agent is associated with, or linked to, the modified TCR-therapeutic agent conjugate.

* * * * *